(12) United States Patent
Krogstad et al.

(10) Patent No.: US 11,059,817 B2
(45) Date of Patent: Jul. 13, 2021

(54) POTENT ANTIVIRAL PYRAZOLOPYRIDINE COMPOUNDS

(71) Applicant: The Regents of the University of California, Oakland, CA (US)

(72) Inventors: Paul Krogstad, Los Angeles, CA (US); Michael E. Jung, Los Angeles, CA (US); Jun Zuo, Los Angeles, CA (US); Yanpeng Xing, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/763,073

(22) PCT Filed: Sep. 22, 2016

(86) PCT No.: PCT/US2016/053166
§ 371 (c)(1),
(2) Date: Mar. 23, 2018

(87) PCT Pub. No.: WO2017/053604
PCT Pub. Date: Mar. 30, 2017

(65) Prior Publication Data
US 2018/0273527 A1    Sep. 27, 2018

Related U.S. Application Data

(60) Provisional application No. 62/222,629, filed on Sep. 23, 2015, provisional application No. 62/222,625, filed on Sep. 23, 2015.

(51) Int. Cl.
*C07D 471/04*    (2006.01)
*A61P 31/12*    (2006.01)
*A61P 31/14*    (2006.01)

(52) U.S. Cl.
CPC ............ *C07D 471/04* (2013.01); *A61P 31/12* (2018.01); *A61P 31/14* (2018.01)

(58) Field of Classification Search
USPC ......................................................... 514/303
See application file for complete search history.

(56) References Cited

U.S. PATENT DOCUMENTS

| | | | |
|---|---|---|---|
| 2008/0058326 A1 | 3/2008 | Hartung et al. | |
| 2008/0182844 A1* | 7/2008 | Bjergarde | C07D 471/04 514/234.2 |
| 2012/0277233 A1* | 11/2012 | Tao | C07D 401/04 514/236.2 |

(Continued)

FOREIGN PATENT DOCUMENTS

| | | |
|---|---|---|
| JP | 2009-196932 A | 9/2009 |
| WO | WO-2010/100475 A1 | 9/2010 |

(Continued)

OTHER PUBLICATIONS

Chemical Abstracts Registry database, record for RN 1325107-93-4, entered into database on Aug. 29, 2011. (Year: 2011).*

(Continued)

*Primary Examiner* — Daniel R Carcanague
(74) *Attorney, Agent, or Firm* — Foley & Lardner LLP

(57) ABSTRACT

The present technology provides compounds according to Formulas (I), (II), or (III) useful in inhibiting an enterovirus, paramyxovirus, respiratory virus, flaviviridae virus, bunyaviridae virus, togaviridae virus, or rabies virus in a cell and/or treating subjects suffering from an enterovirus, paramyxovirus, respiratory virus, flaviviridae virus, bunyaviridae virus, togaviridae virus, or rabies virus.

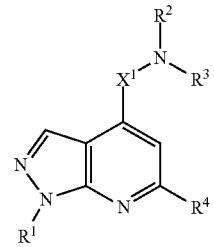

(I)

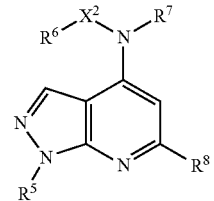

(II)

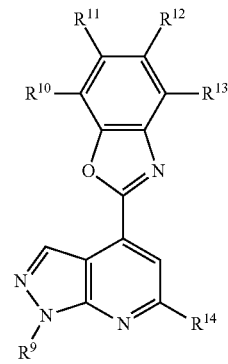

(III)

20 Claims, No Drawings

(56) References Cited

U.S. PATENT DOCUMENTS

| | | | |
|---|---|---|---|
| 2015/0164910 A1 | 6/2015 | Krogstad et al. | |
| 2020/0223842 A1* | 7/2020 | Krogstad | C07D 471/04 |

FOREIGN PATENT DOCUMENTS

| | | |
|---|---|---|
| WO | WO-2011/000566 A2 | 1/2011 |
| WO | WO-2011/140325 A1 | 11/2011 |
| WO | WO-2013/087744 A1 | 6/2013 |
| WO | WO-2013123071 A1 * | 8/2013 |
| WO | WO-2013188848 A2 * | 12/2013 ........... A61K 31/437 |

OTHER PUBLICATIONS

Zuo; Antimicrobial Agents and Chemotherapy 2016, 60, 1615-1626. (Year: 2016).*
Xing; J. Med. Chem. 2018, 61,4, 1688-1703. (Year: 2018).*
National Center for Biotechnology Information. PubChem Database. MolPort-010-451-295, SID=163897465, Deposited Sep. 10, 2013. https://pubchem.ncbi.nlm.nih.gov/substance/163897465 (accessed on Mar. 25, 2019) (Year: 2013).*
National Center for Biotechnology Information. PubChem Database. MCULE-7220586393, Source=Mcule, SID=167159515, https://pubchem.ncbi.nlm.nih.gov/substance/167159515 (accessed on Jul. 16, 2019) Available on Dec. 2, 2013. (Year: 2013).*
National Center for Biotechnology Information. PubChem Database. SID 135538643, Source=ChemBridge, SID=135538643, https://pubchem.ncbi.nlm.nih.gov/substance/135538643 (accessed on Jul. 16, 2019) Available on Mar. 30, 2012. (Year: 2012).*
Chemical Abstracts STN Registry Database, Record for RN 1089634-70-7, "1-(1-methylethyl)-N-4-pyridinyl-6-(2-thienyl)-1H-pyrazolo[3,4-b]pyridine-4-carboxamide", entered into STN Dec. 24, 2008. (Year: 2008).*
Chemical Abstracts STN Registry Database, Record for RN 931087-72-8, "6-cyclopropyl-1-(1-methylethyl)-N-3-pyridinyl-1H-pyrazolo[3,4-b]pyridine-4-carboxamide", entered into STN Apr. 20, 2007. (Year: 2007).*
Chemical Abstracts STN Registry Database, Record for RN 1288184-03-1, "N-(5-fluoro-2-pyridinyl)-6-(2-furanyl)-1-(1-methylethyl)-1H-pyrazolo[3,4-b]pyridine-4-carboxamide", entered into STN May 1, 2011. (Year: 2011).*
Chemical Abstracts STN Registry Database, Record for RN 941087-11-2, "6-cyclopropyl-N-(4-fluorophenyl)-1-(1-methylethyl)-1H-pyrazolo[3,4-b]pyridine-4-carboxamide", entered into STN Jul. 4, 2007. (Year: 2007).*
Chemical Abstracts STN Registry Database record for RN 920836-33-5, entered on Feb. 14, 2007. (Year: 2007).*
Chemical Abstracts STN Registry Database record for RN 1252534-35-2, entered on Nov. 10, 2010. (Year: 2010).*
Chemical Abstracts STN Registry Database, Record for RN 1325869-59-7, entered into STN Aug. 31, 2011. (Year: 2011).*
Chemical Abstracts STN Registry Database, Record for RN 1090478-05-9, entered into STN Dec. 26, 2008. (Year: 2008).*
Chemical Abstracts STN Registry Database, Record for RN 931087-72-8, entered into STN Apr. 20, 2007. (Year: 2007).*
Chemical Abstracts STN Registry Database, Record for RN 927140-76-9, entered into STN Mar. 18, 2007. (Year: 2007).*
Chemical Abstracts STN Registry Database, Record for RN 1089596-75-7, entered into STN Dec. 24, 2008. (Year: 2008).*
Chemical Abstracts STN Registry Database, Record for RN 1010546-14-1, entered into STN Mar. 28, 2008. (Year: 2008).*
Chemical Abstracts STN Registry Database, Record for RN 1648209-32-8, entered into STN Feb. 16, 2015. (Year: 2015).*
National Center for Biotechnology Information. PubChem Substance Record for SID 106014121, AKOS001466915, Source: AKos Consulting & Solutions. Available Feb. 22, 2011. Retrieved Oct. 12, 2020 from https://pubchem.ncbi.nlm.nih.gov/substance/106014121. (Year: 2011).*
National Center for Biotechnology Information. PubChem Compound Summary for CID 16961323. Create Date Nov. 13, 2007. Retrieved Oct. 12, 2020 from https://pubchem.ncbi.nlm.nih.gov/compound/16961323. (Year: 2007).*
National Center for Biotechnology Information. PubChem Substance Record for SID 177285169, AB00784482-01, Source: Southern Research Institute. Available May 20, 2014. Retrieved Oct. 12, 2020 from https://pubchem.ncbi.nlm.nih.gov/substance/177285169. (Year: 2014).*
National Center for Biotechnology Information. PubChem Substance Record for SID 177282882, AB00785372-01, Source: Southern Research Institute. Available May 20, 2014. Retrieved Oct. 12, 2020 from https://pubchem.ncbi.nlm.nih.gov/substance/177282882. (Year: 2014).*
National Center for Biotechnology Information. PubChem Compound Summary for CID 52871211. Create Date May 20, 2011. Retrieved Oct. 12, 2020 from https://pubchem.ncbi.nlm.nih.gov/compound/52871211. (Year: 2011).*
National Center for Biotechnology Information. PubChem Compound Summary for CID 17501846. Create Date Nov. 13, 2007. Retrieved Oct. 12, 2020 from https://pubchem.ncbi.nlm.nih.gov/compound/17501846. (Year: 2007).*
Chemical Abstracts STN Registry Database, Record for RN 949386-39-4, "N-(4-Fluorophenyl)-6-(furan-2-yl)-1-isopropyl-1H-pyrazolo[3,4-b]pyridine-4-carboxamide", entered into STN Oct. 5, 2007. (Year: 2007).*
Chemical Abstracts STN Registry Database, Record for RN 949346-97-8, "N-(3,4-difluorophenyl)-6-(2-furanyl)-1-(1-methylethyl)-1H-Pyrazolo[3,4-b]pyridine-4-carboxamide", entered into STN Oct. 5, 2007. (Year: 2007).*
Chemical Abstracts STN Registry Database, Record for RN 949639-94-5, "6-(2-furanyl)-1-(1-methylethyl)-N-(3-nitrophenyl)-1H-Pyrazolo[3,4-b]pyridine-4-carboxamide", entered into STN Oct. 9, 2007. (Year: 2007).*
National Center for Biotechnology Information. PubChem Substance Record for SID 133085152, AKOS006802525, Source: AKos Consulting & Solutions, https://pubchem.ncbi.nlm.nih.gov/substance/133085152. Accessed Jan. 19, 2021. Deposit Date Jan. 25, 2012. (Year: 2012).*
STN Registry Record for RN 927140-76-9, Entered STN on Mar. 18, 2007. (Year: 2007).*
STN Registry Record for RN 949767-35-5, Entered STN on Oct. 9, 2007. (Year: 2007).*
STN Registry Record for RN 1010953-00-0, Entered STN on Mar. 30, 2008. (Year: 2008).*
STN Registry Record for RN 1277865-76-5, Entered STN on Apr. 10, 2011. (Year: 2011).*
STN Registry Record for RN 1010633-66-5, Entered STN on Mar. 28, 2008. (Year: 2008).*
STN Registry Record for RN 931052-94-7, Entered STN on Apr. 19, 2007. (Year: 2007).*
STN Registry Record for RN 938757-59-6, Entered STN on Jun. 24, 2007. (Year: 2007).*
National Center for Biotechnology Information. PubChem Compound Summary for CID 46677301. https://pubchem.ncbi.nlm.nih.gov/compound/46677301. Create Date Jul. 23, 2010. (Year: 2010).*
Chemical Abstracts STN Registry Database, record for RN 1011000-68-2, entered on Mar. 30, 2008. (Year: 2008).*
De Palma, A.M. et al. (2008) "Selective Inhibitors of Picornavirus Replication," Medicinal Research Reviews 28(6):823-884.
International Search Report (ISA/KR) for International Application No. PCT/US2013/046024, dated Nov. 27, 2013, 4 pages.
STN Registration No. RN 949764-03-8., Entered into database on Oct. 9, 2007.
STN Registration No. RN 949808-59-7., Entered into database on Oct. 9, 2007.
U.S. Office Action dated Mar. 24, 2016, from U.S. Appl. No. 14/407,665.
U.S. Office Action dated Nov. 9, 2016, from U.S. Appl. No. 14/407,665.
International Search Report and Written Opinion dated Jan. 5, 2017, from application No. PCT/US2016/053166.
"CAS Registry and CAS Registry Number FAQs" (accessed Mar. 8, 2019), from https://www.cas.org/support/documentation/chemical-substances/faqs.

(56) References Cited

OTHER PUBLICATIONS

Ulferts et al. (2013) "Selective Serotonin Reuptake Inhibitor Fluoxetine Inhibits Replication of Human Enteroviruses B and D by Targeting Viral Protein 2C," Antimicrobial Agents and Chemotherapy, vol. 57, No. 4, pp. 1952-1956.

Zuo et al. (2016) "Discovery of Structurally Diverse Small-Molecule Compounds with Broad Antiviral Activity against Enteroviruses," Antimicrobial Agents and Chemotherapy, vol. 60, No. 3, pp. 1615-1626.

* cited by examiner

POTENT ANTIVIRAL PYRAZOLOPYRIDINE COMPOUNDS

CROSS-REFERENCE TO RELATED APPLICATIONS

This application is a national stage application under 35 U.S.C. § 371 of International Application No. PCT/US2016/053166, filed Sep. 22, 2016, which in turn claims priority under § 35 U.S.C. 119(e) to U.S. Provisional Patent Application No. 62/222,625, filed Sep. 23, 2015, and U.S. Provisional Patent Application No. 62/222,629, filed Sep. 23, 2015, the entire disclosures of each of which are hereby incorporated by reference in their entireties for any and all purposes.

U.S. GOVERNMENT LICENSE RIGHTS

This invention was made with Government support under Grant Number AI107383, awarded by the National Institutes of Health. The Government has certain rights in the invention.

FIELD

The present technology generally relates to compounds useful in inhibiting an enterovirus, paramyxovirus, respiratory virus, flaviviridae virus, bunyaviridae virus, togaviridae virus, or rabies virus in cells and/or treating subjects suffering from an enterovirus, paramyxovirus, respiratory virus, flaviviridae virus, bunyaviridae virus, togaviridae virus, or rabies virus.

BACKGROUND

Throughout this disclosure, various publications, patents and published patent specifications are referenced by an identifying citation. Also within this disclosure are Arabic numerals referring to referenced citations, the full bibliographic details of which are provided immediately preceding the claims. The disclosures of these publications, patents and published patent specifications are hereby incorporated by reference into the present disclosure to more fully describe the state of the art to which this invention pertains.

The human enteroviruses (EVs) are a genus of more than 110 serologically distinct, small, non-enveloped RNA viruses responsible for poliomyelitis, encephalitis, acute heart failure, fulminant sepsis in newborns, and other life-threatening infections (Cherry, J. D. et al. (2009) Enteroviruses and Parechoviruses, in Textbook of Pediatric Infectious Diseases, R. D. Feigin, et al., Editors. 2009, WB Saunders Co: Philadelphia, Pa.: 1984-2041). While immunization has curtailed circulation of the polioviruses in most of the world, other EVs (coxsackieviruses, echoviruses, and numbered EVs) continue to cause substantial morbidity and mortality.

For example, enterovirus 71 (EV71) has been the cause of numerous epidemics of central nervous system infection in Europe and the Asia-Pacific Region over the last 15 years (McMinn, P. et al. (2001) Clin Infect Dis. 32(2):236-242; McMinn, P. C. (2002) FEMS Microbiol Rev. 26(1):91-107), including an outbreak earlier in 2012 in Cambodia that caused more than 60 deaths (Seiff, A. (2012) Lancet 380 (9838):206). A recent outbreak of coxsackievirus B1 (CVB1) myocarditis in the United States also highlighted the mutability of enteroviruses and their epidemic potential. A new variant of CVB1 emerged in 2007 that was detected at nearly 50 sites in the U.S. linked to clusters of cases of sepsis, myocarditis, and deaths among newborns (Verma, N. A. et al. (2009) Clin Infect Dis. 49(5):759-763; Wikswo, M. E. et al. (2009) Clin Infect Dis. 49(5):e44-e51). In 2011 and 2012, cases of severe Hand, Foot, and Mouth Disease associated with coxsackievirus A6 requiring hospitalization were reported in four states.

SUMMARY

In an aspect, a compound represented by Formula I is provided

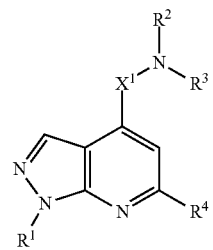

(I)

or a pharmaceutically acceptable salt thereof, where $R^1$ is H, alkyl, cycloalkyl, heterocyclyl, aryl, or heteroaryl; $R^2$ is a substituted or unsubstituted aryl group or a substituted or unsubstituted heteroaryl group; $R^3$ is H or $C_1$-$C_6$ alkyl; or —N($R^2$)($R^3$) is a substituted or unsubstituted aryl-fused non-aromatic heterocyclyl group or a substituted or unsubstituted heteroaryl-fused non-aromatic heterocyclyl group; and $R^4$ is a substituted or unsubstituted cycloalkyl, aryl, or heteroaryl, and $X^1$ is —C(O)—, —C(NH)—, —C(S)—, or —S(O)$_2$—. In any embodiment herein, it may be that in Formula I $R^1$ is H, alkyl, cycloalkyl, or aryl; $R^2$ is a substituted or unsubstituted heteroaryl group or a substituted aryl group where the substituents of the aryl group are selected from the group consisting of a halogen, a nitro group, an alkanoyl group, a carbamoyl group, an ester, an amido group, a sulfone group, a sulfonyl group, sulfonamido group, and a trifluoromethyl group; and $R^3$ is hydrogen, or —N($R^2$)($R^3$) is a substituted or unsubstituted indolinyl group; $R^4$ is a substituted or unsubstituted cycloalkyl, phenyl, or heteroaryl; and $X^1$ is —C(O)—, —C(NH)—, —C(S)—, or —S(O)$_2$—; provided that where $R^1$ is isopropyl, $R^3$ is hydrogen, $R^4$ is 2-thiophenyl, and $X^1$ is —C(O)—, $R^2$ is not 2-fluorophenyl or 2-chloro-4-fluorophenyl.

In a related aspect, a compound according to Formula II is provided:

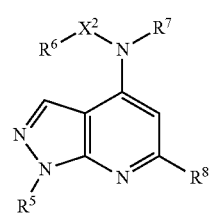

(II)

or a pharmaceutically acceptable salt thereof, where $R^5$ is H or a substituted or unsubstituted alkyl, cycloalkyl, or aryl group; $R^6$ is a substituted or unsubstituted aryl, heteroaryl, or aryloyl group; and $R^7$ is H or a substituted or unsubstituted aryl, heteroaryl, or aryloyl group; R⁸ is a substituted or unsubstituted cycloalkyl, phenyl, or heteroaryl; and X² is —C(O)—, —C(NH)—, —C(S)—, or —S(O)₂—.

In a further related aspect, a compound according to Formula III is provided:

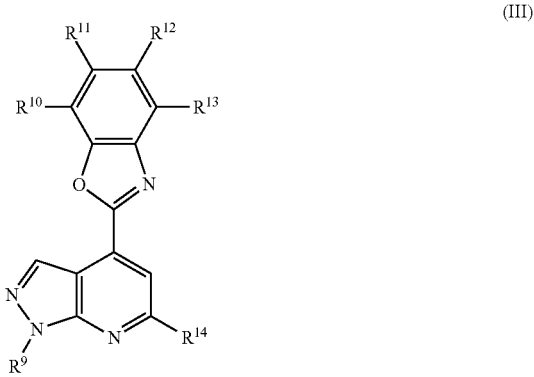

or a pharmaceutically acceptable salt thereof, where R⁹ is H or a substituted or unsubstituted alkyl, cycloalkyl, or aryl group; R¹⁰, R¹¹, R¹², and R¹³ are each independently H, halogen, nitro, alkanoyl, carbamoyl, ester, amido, sulfone, sulfonyl, sulfonamido, or trifluoromethyl; and R¹⁴ is a substituted or unsubstituted cycloalkyl, phenyl, or heteroaryl.

In an aspect, a composition is provided that includes a compound of Formulas I-III and a pharmaceutically acceptable carrier.

In an aspect, a pharmaceutical composition for treating an enterovirus, paramyxovirus, respiratory virus, flaviviridae virus, bunyaviridae virus, togaviridae virus, or rabies virus infection is provided where the composition includes an effective amount of a compound of any one of Formulas I-III and a pharmaceutically acceptable excipient.

In an aspect, a method for inhibiting the replication of an enterovirus, paramyxovirus, respiratory virus, flaviviridae virus, bunyaviridae virus, togaviridae virus, or rabies virus in a cell infected with the enterovirus, paramyxovirus, respiratory virus, flaviviridae virus, bunyaviridae virus, togaviridae virus, or rabies virus is provided. The method includes contacting the cell with a compound of any one of Formulas I-III of the present technology.

In an aspect, a method of inhibiting death of a cell infected with an enterovirus, paramyxovirus, respiratory virus, flaviviridae virus, bunyaviridae virus, togaviridae virus, or rabies virus, the method comprising contacting the cell with a compound of any one of Formulas I-III.

In an aspect, a method of treating a patient or animal infected with an enterovirus, paramyxovirus, respiratory virus, flaviviridae virus, bunyaviridae virus, togaviridae virus, or rabies virus is provided, the method including administration of an effective amount of a compound of any one of the above embodiments of the present technology to the patient or animal. In the method, administration of the effective amount of a compound of Formulas I-III to the patient or animal treats the patient or animal infected with the enterovirus, paramyxovirus, respiratory virus, flaviviridae virus, bunyaviridae virus, togaviridae virus, or rabies virus.

DETAILED DESCRIPTION

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, C¹⁴, P³² and S³⁵ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., SF₅), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Cycloalkyl groups may be substituted or unsubstituted. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Cycloalkylalkyl groups may be substituted or unsubstituted. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Alkenyl groups may be substituted or unsubstituted. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Alkynyl groups may be substituted or unsubstituted. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Aryl groups may be substituted or unsubstituted. The phrase "aryl groups" includes groups containing fused rings, such as fused aromatic-aliphatic ring systems (e.g., indanyl, tetrahydronaphthyl, and the like). Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be monosubstituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Heteroaryl groups may be substituted or unsubstituted. Thus, the phrase "heteroaryl groups" includes fused ring compounds as well as includes heteroaryl groups that have other groups bonded to one of the ring members, such as alkyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene. Such groups may further be substituted or unsubstituted.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The terms "alkanoyl" and "alkanoyloxy" as used herein can refer, respectively, to —C(O)-alkyl and —O—C(O)-alkyl groups, where in some embodiments the alkanoyl or alkanoyloxy groups each contain 2-5 carbon atoms. Similarly, the terms "aryloyl" and "aryloyloxy" respectively refer to —C(O)-aryl and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylic acid" as used herein refers to a compound with a —C(O)OH group. The term "carboxylate" as used herein refers to a —C(O)O⁻ group. A "protected carboxylate" refers to a —C(O)O-G where G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "ester" as used herein refers to —COOR$^{70}$ groups. R$^{70}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{15}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{80}$ groups, sulfoxides include —S(O)R$^{81}$ groups, sulfones include —SO$_2$R$^{82}$ groups, and sulfonyls include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl, aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "trifluoromethyldiazirido" refers to

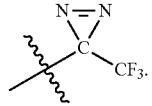

The term "isocyano" refers to —NC.
The term "isothiocyano" refers to —NCS.
The term "pentafluorosulfanyl" refers to —SF$_5$.

The phrase "selectively treats" as used herein will be understood by persons of ordinary skill in the art and will vary to some extent depending upon the context in which the phrase is used. If there are uses of the phrase which are not clear to persons of ordinary skill in the art, given the context in which the phrase is used, the phrase at minimum refers to the compounds acting through a viral-specific mechanism of action, resulting in fewer off-target effects because the compounds target the virus and not the host.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

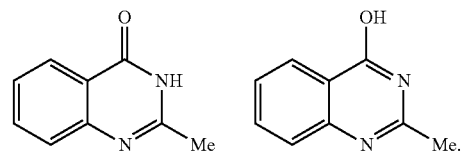 [SMILES: Cc1nc2ccccc2c(=O)[nH]1 ; Cc1nc(O)c2ccccc2n1]

As another example, guanidines may exhibit the following isomeric forms in protic organic solution, also referred to as tautomers of each other:

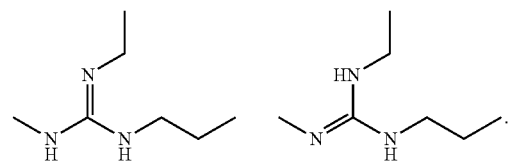

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

The present technology provides compounds unlike any previously described inhibitors of enterovirus replication. Compared to previous inhibitors, the compounds of the present technology are more potent inhibitors of various enteroviruses. Furthermore, the compounds of the present technology are inhibitors of paramyxoviruses, respiratory viruses, flaviviridae viruses, bunyaviridae viruses, and togaviridae viruses.

Accordingly, in an aspect, a compound represented by Formula I is provided

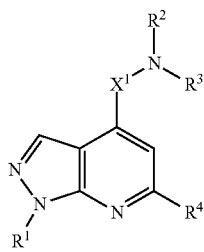

(I)

or a pharmaceutically acceptable salt thereof, where $R^1$ is H, alkyl, cycloalkyl, heterocyclyl, aryl, or heteroaryl; $R^2$ is a substituted or unsubstituted aryl group or a substituted or unsubstituted heteroaryl group; $R^3$ is H or $C_1$-$C_6$ alkyl; or —N($R^2$)($R^3$) is a substituted or unsubstituted aryl-fused non-aromatic heterocyclyl group or a substituted or unsubstituted heteroaryl-fused non-aromatic heterocyclyl group; and $R^4$ is a substituted or unsubstituted cycloalkyl, aryl, or heteroaryl, and $X^1$ is —C(O)—, —C(NH)—, —C(S)—, or —S(O)$_2$—. In any embodiment herein, it may be that in Formula I $R^1$ is H, alkyl, cycloalkyl, or aryl; $R^2$ is a substituted or unsubstituted heteroaryl group or a substituted aryl group where the substituents of the aryl group are selected from the group consisting of a halogen, a nitro group, an alkanoyl group, a carbamoyl group, an ester, an amido group, a sulfone group, a sulfonyl group, sulfonamido group, and a trifluoromethyl group; and $R^3$ is hydrogen, or —N($R^2$)($R^3$) is a substituted or unsubstituted indolinyl group; $R^4$ is a substituted or unsubstituted cycloalkyl, phenyl, or heteroaryl; and $X^1$ is —C(O)—, —C(NH)—, —C(S)—, or —S(O)$_2$—; provided that where $R^1$ is isopropyl, $R^3$ is hydrogen, $R^4$ is 2-thiophenyl, and $X^1$ is —C(O)—, $R^2$ is not 2-fluorophenyl or 2-chloro-4-fluorophenyl. $R^1$ may be a substituted or unsubstituted $C_1$-$C_6$ alkyl, unsubstituted $C_4$-$C_7$ cycloalkyl, or a substituted phenyl group. In any of the above embodiments, $R^2$ may be a heteroaryl group, preferably a six-membered nitrogen-containing heteroaryl group. In any of the above embodiments, $R^2$ may be a substituted aryl group where the aryl group bears 1, 2, or 3 substituents. In any of the above embodiments, $R^2$ may be a substituted aryl group where the substituents are selected from the group consisting of a halogen, a nitro group, cyano group, an alkanoyl group, a carbamoyl group, an ester, a sulfonyl group, a sulfonamido group, and a trifluoromethyl group. In some embodiments, $R^2$ is fluorophenyl, difluorophenyl, trifluorophenyl, sulfonamidophenyl, amidophenyl, or trifluormethylphenyl. $R^4$ may be a substituted or unsubstituted thiophenyl group in any of the above embodiments.

As discussed above, —N($R^2$)($R^3$) may be a substituted or unsubstituted aryl-fused non-aromatic heterocyclyl group or substituted or unsubstituted heteroaryl-fused non-aromatic heterocyclyl group. Examples include, but are not limited to, the following groups:

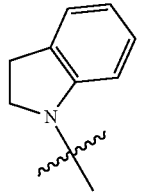

i

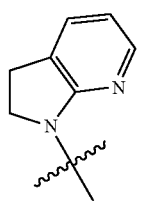

ii

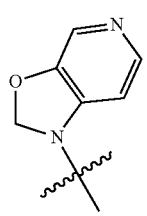

iii

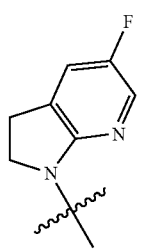

iv

In any embodiment herein, it may be —N($R^2$)($R^3$) is a substituted or unsubstituted indolin-1yl group or a substituted or unsubstituted 2,3-dihydro-1H-pyrrolo[2,3-b]pyridin-1-yl group. An example of the present technology where —N($R^2$)($R^3$) is a substituted indolinyl group includes JX-048. An example where —N($R^2$)($R^3$) is an unsubstituted 2,3-dihydro-1H-pyrrolo[2,3-b]pyridin-1-yl group (exemplified by ii in the list above) includes JX-076.

The compound of Formula I may be a compound selected from any one of the compounds listed in Table 1 below.

TABLE 1

| Cmpd # | $R^1$ | $R^2$ | $R^3$ | $R^4$ | $X^1$ |
|---|---|---|---|---|---|
| JX-001 | ![Me-CH-Me] | ![2,4-difluorophenyl] | H | ![thiophenyl] | —C(O)— |

TABLE 1-continued

| Cmpd # | R¹ | R² | R³ | R⁴ | X¹ |
|---|---|---|---|---|---|
| JX-002 | iPr (CHMe₂) | 2-F-phenyl | H | phenyl | —C(O)— |
| JX-003 | iPr (CHMe₂) | 2-F-phenyl | H | pyridin-4-yl | —C(O)— |
| JX-004 | iPr (CHMe₂) | 2-F-phenyl | H | pyridin-2-yl | —C(O)— |
| JX-005 | iPr (CHMe₂) | 2-F-phenyl | H | pyridin-3-yl | —C(O)— |
| JX-007 | iPr (CHMe₂) | 2-F-phenyl | H | thiazol-2-yl | —C(O)— |
| JX-010 | iPr (CHMe₂) | 2-F-phenyl | H | thiazol-5-yl | —C(O)— |
| JX-011 | iPr (CHMe₂) | 2-F-phenyl | H | oxazol-5-yl | —C(O)— |
| JX-012 | phenyl | 2-F-phenyl | H | thien-2-yl | —C(O)— |

TABLE 1-continued
| Cmpd # | R¹ | R² | R³ | R⁴ | X¹ |
|---|---|---|---|---|---|
| JX-013 | 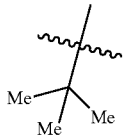 | 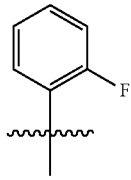 [SMILES: *c1ccccc1F] | H | 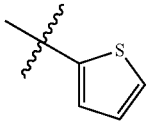 [SMILES: *c1cccs1] | —C(O)— |
| JX-014 | 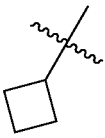 [SMILES: *C1CCC1] | 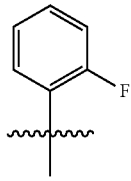 | H | 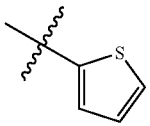 [SMILES: *c1cccs1] | —C(O)— |
| JX-022 | 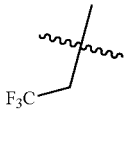 | 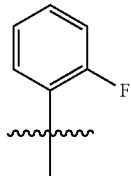 [SMILES: *c1ccccc1F] | H | 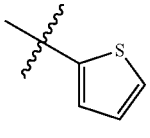 [SMILES: *c1cccs1] | —C(O)— |
| JX-017 | 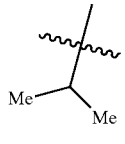 | 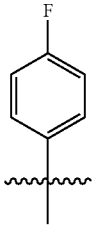 | H | 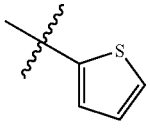 | —C(O)— |
| JX-021 | 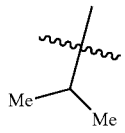 | 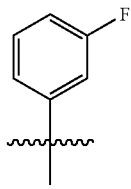 [SMILES: *c1cccc(F)c1] | H | 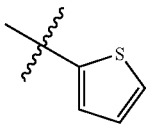 [SMILES: *c1cccs1] | —C(O)— |
| JX-008 | 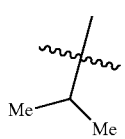 | 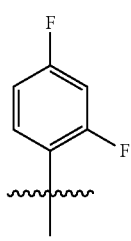 [SMILES: *c1ccc(F)cc1F] | H | 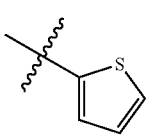 | —C(O)— |
| JX-009 | 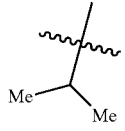 | 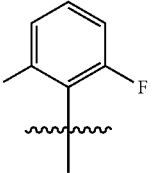 | H | 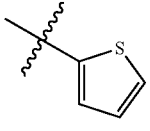 [SMILES: *c1cccs1] | —C(O)— |

TABLE 1-continued

| Cmpd # | R¹ | R² | R³ | R⁴ | X¹ |
|---|---|---|---|---|---|
| JX-015 | isopropyl | 3,4-difluorophenyl | H | thiophen-2-yl | —C(O)— |
| JX-016 | isopropyl | 3,5-difluorophenyl | H | thiophen-2-yl | —C(O)— |
| JX-018 | isopropyl | 2,5-difluorophenyl | H | thiophen-2-yl | —C(O)— |
| JX-019 | isopropyl | 2,3-difluorophenyl | H | thiophen-2-yl | —C(O)— |
| JX-020 | isopropyl | 3,4,5-trifluorophenyl | H | thiophen-2-yl | —C(O)— |
| JX-023 | isopropyl | 2-(trifluoromethyl)phenyl | H | thiophen-2-yl | —C(O)— |
| JX-024 | isopropyl | 4-(trifluoromethyl)phenyl | H | thiophen-2-yl | —C(O)— |

TABLE 1-continued

| Cmpd # | R¹ | R² | R³ | R⁴ | X¹ |
|---|---|---|---|---|---|
| JX-006 | isopropyl | 4-(SO₂NH₂)-phenyl | H | thiophen-2-yl | —C(O)— |
| JX-025 | isopropyl | 3-(SO₂NH₂)-phenyl | H | thiophen-2-yl | —C(O)— |
| JX-033 | isopropyl | 2-(SO₂NH₂)-phenyl | H | thiophen-2-yl | —C(O)— |
| JX-027 | cyclopentyl | 4-F-phenyl | H | thiophen-2-yl | —C(O)— |
| JX-028 | cyclohexyl | 4-F-phenyl | H | thiophen-2-yl | —C(O)— |
| JX-029 | cycloheptyl | 4-F-phenyl | H | thiophen-2-yl | —C(O)— |
| JX-030 | isopropyl | 4-F-phenyl | H | thiophen-3-yl | —C(O)— |

TABLE 1-continued

| Cmpd # | R¹ | R² | R³ | R⁴ | X¹ |
|---|---|---|---|---|---|
| JX-031 | 4-methoxybenzyl | 4-fluorophenyl | H | 2-thienyl | —C(O)— |
| JX-032 | H | 4-fluorophenyl | H | 2-thienyl | —C(O)— |
| JX-026 | isopropyl | 4-fluorophenyl | H | 2-furyl | —C(O)— |
| JX-038 | isopropyl | 4-fluorophenyl | H | cyclopropyl | —C(O)— |
| JX-040 | isopropyl | 2-pyridyl | H | 2-thienyl | —C(O)— |
| JX-041 | isopropyl | 2-pyrimidinyl | H | 2-thienyl | —C(O)— |
| JX-042 | isopropyl | 4-pyridyl | H | 2-thienyl | —C(O)— |

TABLE 1-continued

| Cmpd # | R¹ | R² | R³ | R⁴ | X¹ |
|---|---|---|---|---|---|
| JX-043 | isopropyl | pyrimidin-4-yl | H | thiophen-2-yl | —C(O)— |
| JX-045 | isopropyl | 6-(thiophen-2-yl)-1-isopropyl-1H-pyrazolo[3,4-b]pyridin-4-yl | H | thiophen-2-yl | —C(O)— |
| JX-046 | isopropyl | 4-fluorophenyl | H | thiophen-2-yl | —C(S)— |
| JX-047 | isopropyl | 4-(methylsulfonyl)phenyl | H | thiophen-2-yl | —C(O)— |
| JX-048 | isopropyl | (5-fluoro-substituted aryl, propyl-linked) | H | thiophen-2-yl | —C(O)— |
| JX-049 | isopropyl | 6-fluoropyridin-3-yl | H | thiophen-2-yl | —S(O)₂— |

TABLE 1-continued

| Cmpd # | R¹ | R² | R³ | R⁴ | X¹ |
|---|---|---|---|---|---|
| JX-050 | iPr (CHMe₂) | 4-fluoro-2-bromophenyl | H | thiophen-2-yl | —C(O)— |
| JX-052 | iPr (CHMe₂) | 3-(SO₂NMe₂)phenyl | H | thiophen-2-yl | —C(O)— |
| JX-053 | iPr (CHMe₂) | 3-(SO₂NHMe)phenyl | H | thiophen-2-yl | —C(O)— |
| JX-055 | iPr (CHMe₂) | 3-(SO₂NH₂)phenyl | H | cyclopropyl | —C(O)— |
| JX-056 | iPr (CHMe₂) | pyridin-3-yl | H | thiophen-2-yl | —C(O)— |
| JX-057 | iPr (CHMe₂) | pyridin-2-yl | H | thiophen-3-yl | —C(O)— |
| JX-058 | iPr (CHMe₂) | pyrimidin-2-yl | H | thiophen-3-yl | —C(O)— |
| JX-059 | iPr (CHMe₂) | pyrimidin-4-yl | H | thiophen-3-yl | —C(O)— |

TABLE 1-continued
| Cmpd # | R¹ | R² | R³ | R⁴ | X¹ |
|---|---|---|---|---|---|
| JX-060 | 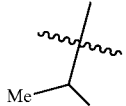 | 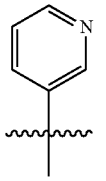 | H | 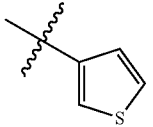 [SMILES: *c1ccsc1] | —C(O)— |
| JX-061 | 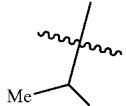 | 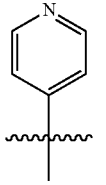 | H | 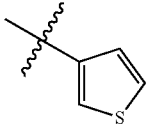 [SMILES: *c1ccsc1] | —C(O)— |
| JX-064 | 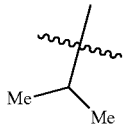 | 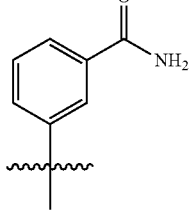 | H | 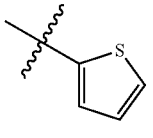 [SMILES: *c1cccs1] | —C(O)— |
| JX-065 | 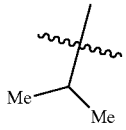 | 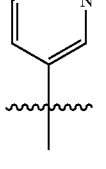 | H | 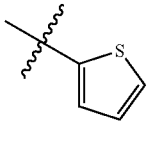 | —C(NH)— |
| JX-066 | 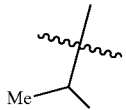 | 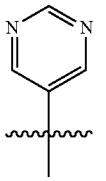 | H | 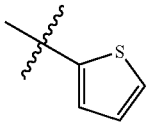 [SMILES: *c1cccs1] | —C(O)— |
| JX-067 | 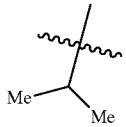 | 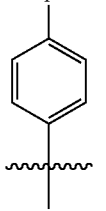 | H | 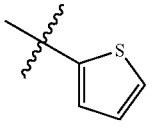 [SMILES: *c1cccs1] | —C(NH)— |
| JX-068 | 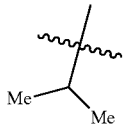 | 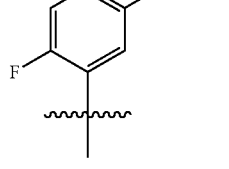 | H | 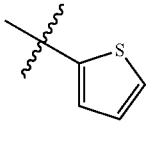 | —C(O)— |

TABLE 1-continued

| Cmpd # | R¹ | R² | R³ | R⁴ | X¹ |
|---|---|---|---|---|---|
| JX-069 | isopropyl | 2-fluoro-5-(SO₂NH₂)phenyl | H | 2-thienyl | —C(O)— |
| JX-070 | isopropyl | 2-pyridyl | H | phenyl | —C(O)— |
| JX-071 | isopropyl | 2-pyridyl | H | cyclopropyl | —C(O)— |
| JX-073 | isopropyl | 4-fluoro-3-(C(O)NH₂)phenyl | H | 2-thienyl | —C(O)— |
| JX-074 | isopropyl | 2-pyridyl | Me | 2-thienyl | —C(O)— |
| JX-075 | isopropyl | 5-fluoro-2-pyridyl | H | 2-thienyl | —C(O)— |
| JX-076 | isopropyl | pyridyl (linked via alkyl) | H | 2-thienyl | —C(O)— |

In any of the above embodiments, the compound of Formula I may be a compound selected from any one of the compounds listed in Table 1 below, with the exception of JX-001.

In a related aspect, a compound according to Formula II is provided:

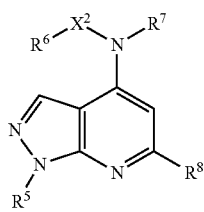

(II)

or a pharmaceutically acceptable salt thereof, where $R^5$ is H or a substituted or unsubstituted alkyl, cycloalkyl, or aryl group; $R^6$ is a substituted or unsubstituted aryl, heteroaryl, or aryloyl group; and $R^7$ is H or a substituted or unsubstituted aryl, heteroaryl, or aryloyl group; $R^8$ is a substituted or unsubstituted cycloalkyl, phenyl, or heteroaryl; and $X^2$ is —C(O)—, —C(NH)—, —C(S)—, or —S(O)$_2$—.

Representative examples of compounds according to Formula II include, but are not limited to, JX-039, JX-044, and JX-054.

JX-039

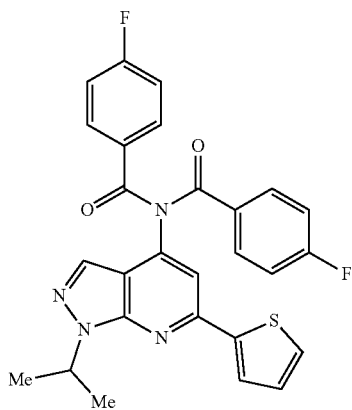

JX-044

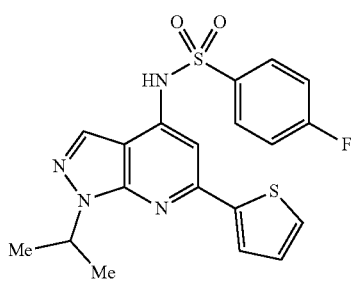

JX-054

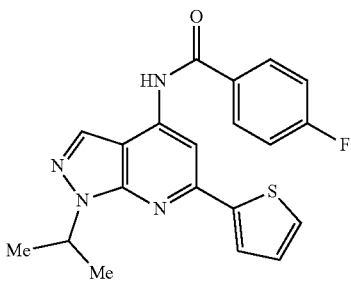

In a further related aspect, a compound according to Formula III is provided:

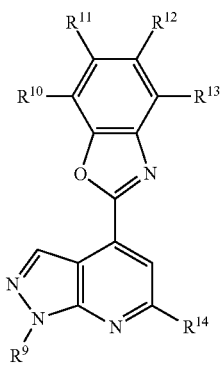

(III)

or a pharmaceutically acceptable salt thereof, where $R^9$ is H or a substituted or unsubstituted alkyl, cycloalkyl, or aryl group; $R^{10}$, $R^{11}$, $R^{12}$, and $R^{13}$ are each independently H, halogen, nitro, alkanoyl, carbamoyl, ester, amido, sulfone, sulfonyl, sulfonamido, or trifluoromethyl; and $R^{14}$ is a substituted or unsubstituted cycloalkyl, phenyl, or heteroaryl. Representative examples of compounds according to Formula III include, but are not limited to, JX-051.

JX-051

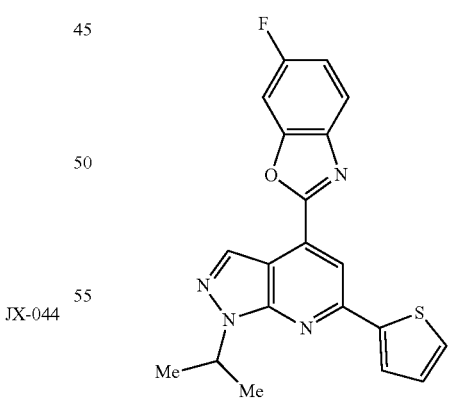

The present technology provides pharmaceutical compositions and medicaments comprising any of one of the embodiments of the compounds of Formulas I-III (or a pharmaceutically acceptable salt thereof) disclosed herein and a pharmaceutically acceptable carrier or one or more excipients or fillers. The compositions may be used in the methods and treatments described herein. The pharmaceutical composition may include an effective amount of any of one of the embodiments of the compounds of the present technology disclosed herein. In any of the above embodiments, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of an enterovirus. Another example of an effective amount includes amounts or dosages that yield acceptable toxicity and bioavailability levels for therapeutic (pharmaceutical) use including, but not limited to, the prophylaxis of an enterovirus. Another example of an effective amount includes amounts or dosages that are capable of reducing symptoms associated with an enterovirus, such as, for example, fever, headache, and/or encephalitis. The effective amount may be from about 0.01 µg to about 1 mg of the compound per gram of the composition, and preferably from about 0.1 µg to about 500 µg of the compound per gram of the composition. As used herein, a "subject" or "patient" is a mammal, such as a cat, dog, rodent or primate. Typically the subject is a human, and, preferably, a human suffering from or suspected of suffering from an enterovirus, paramyxovirus, respiratory virus, flaviviridae virus, bunyaviridae virus, togaviridae virus, or rabies virus, such as Coxsackievirus A9, Coxsackievirus A16, Coxsackievirus B1, Coxsackievirus B2, Coxsackievirus B3-H3, Coxsackievirus B4, Coxsackievirus B5, Enterovirus 68 (also known as Enterovirus D68), Enterovirus 71, Echovirus 6, Echovirus 7, Echovirus 9, Echovirus 11, Echovirus 18, Echovirus 25, Echovirus 30, Poliovirus 1, Poliovirus 3, measles, SARS coronavirus, influenza A H1N1, respiratory syncytial virus, Japanese encephalitis, Powassan virus, Yellow Fever virus, Punta Toro virus, Rift Valley virus, Venezuelan encephalitis virus, or chikungunya virus. The term "subject" and "patient" can be used interchangeably.

In any of the embodiments of the present technology described herein, the pharmaceutical composition may be packaged in unit dosage form. The unit dosage form is effective in treating an enterovirus. Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1 \times 10^{-4}$ g/kg to 1 g/kg, preferably, $1 \times 10^{-3}$ g/kg to 1.0 g/kg. Dosage of a compound of the present technology may also vary from 0.01 mg/kg to 100 mg/kg or, preferably, from 0.1 mg/kg to 10 mg/kg. Suitable unit dosage forms, include, but are not limited to powders, tablets, pills, capsules, lozenges. suppositories. patches. nasal sprays, injectibles, implantable sustained-release formulations, rnucoadherent films, topical varnishes, lipid complexes, etc.

The pharmaceutical compositions may be prepared by mixing one or more compounds of Formulas I-III, pharmaceutically acceptable salts thereof, stereoisomers thereof, tautomers thereof, or solvates thereof, with pharmaceutically acceptable carriers, excipients, binders, diluents or the like to prevent and treat disorders associated with the effects of a viral infection. The compounds and compositions described herein may be used to prepare formulations and medicaments that treat an enterovirus, paramyxovirus, respiratory virus, flaviviridae virus, bunyaviridae virus, togaviridae virus, or rabies virus, such as Coxsackievirus A9, Coxsackievirus A16, Coxsackievirus B1, Coxsackievirus B2, Coxsackievirus B3-H3, Coxsackievirus B4, Coxsackievirus B5, Enterovirus 68 (also known as Enterovirus D68), Enterovirus 71, Echovirus 6, Echovirus 7, Echovirus 9, Echovirus 11, Echovirus 18, Echovirus 25, Echovirus 30, Poliovirus 1, Poliovirus 3, measles, SARS coronavirus, influenza A H1N1, respiratory syncytial virus, Japanese encephalitis, Powassan virus, Yellow Fever virus, Punta Toro virus, Rift Valley virus, Venezuelan encephalitis virus, or chikungunya virus. Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems can be readily employed to determine the therapeutic effectiveness of the treatment according to the present technology.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In an aspect, a method for inhibiting the replication of an enterovirus, paramyxovirus, respiratory virus, flaviviridae virus, bunyaviridae virus, togaviridae virus, or rabies virus in a cell infected with the enterovirus, paramyxovirus, respiratory virus, flaviviridae virus, bunyaviridae virus, togaviridae virus, or rabies virus is provided. The method may include contacting the cell with an effective amount of any one of the above embodiments of compounds of Formulas I-III (or a pharmaceutically acceptable salt thereof). The enterovirus may be Coxsackievirus A9, Coxsackievirus A16, Coxsackievirus B1, Coxsackievirus B2, Coxsackievirus B3-H3, Coxsackievirus B4, Coxsackievirus B5, Enterovirus 68 (also known as Enterovirus D68), Enterovirus 71, Echovirus 6, Echovirus 7, Echovirus 9, Echovirus 11, Echovirus 18, Echovirus 25, Echovirus 30, Poliovirus 1, or Poliovirus 3. The paramyxovirus may be measles. The respiratory virus may be SARS coronavirus, influenza A H1N1, or respiratory syncytial virus. The flaviviridae virus may be Japanese encephalitis, Powassan virus, or Yellow Fever virus. The bunyaviridae virus may be Punta Toro virus or Rift Valley virus. The togaviridae virus may be Venezuelan encephalitis virus or chikungunya virus. In any of the embodiments of the method, the contacting step may include administration of a pharmaceutical composition, where the pharmaceutical composition includes an effective amount of any one of the embodiments of the compounds of Formulas I-III (or a pharmaceutically acceptable salt thereof) and a pharmaceutically acceptable carrier. The effective amount may be from about 0.01 µg to about 1 mg of the compound per gram of the composition, and preferably from about 0.1 µg to about 500 µg of the compound per gram of the composition.

In an aspect, a method of inhibiting death of a cell infected with an enterovirus, paramyxovirus, respiratory virus, flaviviridae virus, bunyaviridae virus, togaviridae virus, or rabies virus is provided, the method including contacting the cell with any one of the above embodiments of the compounds of Formulas I-III (or a pharmaceutically acceptable salt thereof), thereby inhibiting the death of the cell. It may be the method includes contacting the cell with an effective amount of any one of the above embodiments of the compounds of Formulas I-III (or a pharmaceutically acceptable salt thereof). The enterovirus may be Coxsackievirus A9, Coxsackievirus A16, Coxsackievirus B1, Coxsackievirus B2, Coxsackievirus B3-H3, Coxsackievirus B4, Coxsackievirus B5, Enterovirus 68 (also known as Enterovirus D68), Enterovirus 71, Echovirus 6, Echovirus 7, Echovirus 9, Echovirus 11, Echovirus 18, Echovirus 25, Echovirus 30, Poliovirus 1, or Poliovirus 3. The paramyxovirus may be measles. The respiratory virus may be SARS coronavirus, influenza A H1N1, or respiratory syncytial virus. The flaviviridae virus may be Japanese encephalitis, Powassan virus, or Yellow Fever virus. The bunyaviridae virus may be Punta Toro virus or Rift Valley virus. The togaviridae virus may be Venezuelan encephalitis virus or chikungunya virus. In any of the embodiments of the method, the contacting step may include administration of a pharmaceutical composition, where the pharmaceutical composition includes an effective amount of any one of the embodiments of the compounds of Formulas I-III (or a pharmaceutically acceptable salt thereof) and a pharmaceutically acceptable carrier. The effective amount may be from about 0.01 µg to about 1 mg of the compound per gram of the composition, and preferably from about 0.1 µg to about 500 µg of the compound per gram of the composition.

In an aspect, a method of treating a patient or animal infected with an enterovirus, paramyxovirus, respiratory virus, flaviviridae virus, bunyaviridae virus, togaviridae virus, or rabies virus is provided, the method including administration of a compound of any one of the above embodiments of the present technology to the patient or animal. The method may include administration of an effective amount of any one of the embodiments of the compounds of Formulas I-III (or a pharmaceutically acceptable salt thereof). In the method, administration of the compound (e.g., an effective amount of the compound) of any one of the above embodiments of the present technology to the patient or animal treats the patient or animal infected with the enterovirus, paramyxovirus, respiratory virus, flaviviridae virus, bunyaviridae virus, togaviridae virus, or rabies virus. In any embodiment of the method, it may be that administration of the compound of any one of the above embodiments of the present technology selectively treats the enterovirus, paramyxovirus, respiratory virus, flaviviridae virus, bunyaviridae virus, togaviridae virus, or rabies virus. The enterovirus may be Coxsackievirus A9, Coxsackievirus A16, Coxsackievirus B1, Coxsackievirus B2, Coxsackievirus B3-H3, Coxsackievirus B4, Coxsackievirus B5, Enterovirus 68 (also known as Enterovirus D68), Enterovirus 71, Echovirus 6, Echovirus 7, Echovirus 9, Echovirus 11, Echovirus 18, Echovirus 25, Echovirus 30, Poliovirus 1, or Poliovirus 3. The paramyxovirus may be measles. The respiratory virus may be SARS coronavirus, influenza A H1N1, or respiratory syncytial virus. The flaviviridae virus may be Japanese encephalitis, Powassan virus, or Yellow Fever virus. The bunyaviridae virus may be Punta Toro virus or Rift Valley virus. The togaviridae virus may be Venezuelan encephalitis virus or chikungunya virus.

In any of the embodiments of the method of treating a patient or animal infected with an enterovirus, paramyxovirus, respiratory virus, flaviviridae virus, bunyaviridae virus, togaviridae virus, or rabies virus, the method may include administration of a pharmaceutical composition, where the pharmaceutical composition includes an effective amount of any one of the compounds of the present technology or a pharmaceutically acceptable salt thereof and a pharmaceutically acceptable carrier. The effective amount may be from about 0.01 µg to about 1 mg of the compound per gram of the composition, and preferably from about 0.1 µg to about 500 µg of the compound per gram of the composition. In any of the embodiments of the method, the compound or composition may be administered orally, parenterally, rectally, or transdermally.

The examples herein are provided to illustrate advantages of the present technology and to further assist a person of ordinary skill in the art with preparing or using the compounds of the present technology or salts, pharmaceutical compositions, derivatives, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Exemplary Synthetic Procedure

An exemplary, but by no means limiting, synthetic procedure for compounds of the present technology is shown in Scheme 1. $R^1$, $R^2$, $R^3$, and $R^4$ of Scheme 1 are exemplary for Scheme 1 only and not to be confused with or intended to further limit $R^1$, $R^2$, $R^3$, and $R^4$ of Formula I. Condensation of the 1-alkyl-pyrazole-5-amine 1 with the 4-aryl-2,4-diketoester 2 to provides 1H-pyrazolo[3,4-b]pyridine-4-carboxylic ester 3. The components for this coupling reaction are prepared as follows. Formation of the hydrazone 6 may be accomplished by mixing the desired ketone 4 with 3-hydrazinopropanitrile 5. Reaction of 6 with sodium butylate, prepared in situ, is expected to provide the desired 1-alkyl-pyrazole-5-amine 1 (U.S. Pat. No. 5,942,520). This compound could also be prepared by another route, namely reaction of the alkyl hydrazine hydrochloride salt 7 with commercially available 2-chloropropenenitrile 8 to yield 1 (MacKy, M. et al. (2015) Synthesis 47(2):242-248; Ji, N. et al. (2010) Tetrahedron Letters 51(52):6799-6801). The second component 2 may be synthesized by condensation of the aryl methyl ketone 9 with diethyl oxalate 10 to give the product of the Claisen condensation, salt 2 (Chen, H. et al. (2014) Bioorganic & Medicinal Chemistry Letters 24(22): 5251-5255). Addition of 1 and 2 in acetic acid is expected to afford good yields of desired heterocycle 3. Base-mediated hydrolysis of ester of 3 is expected to provide acid 11. Formation of the acid chloride 12 may be followed by addition of the desired aniline 13 and is expected to provide the desired amides.

Scheme 1.
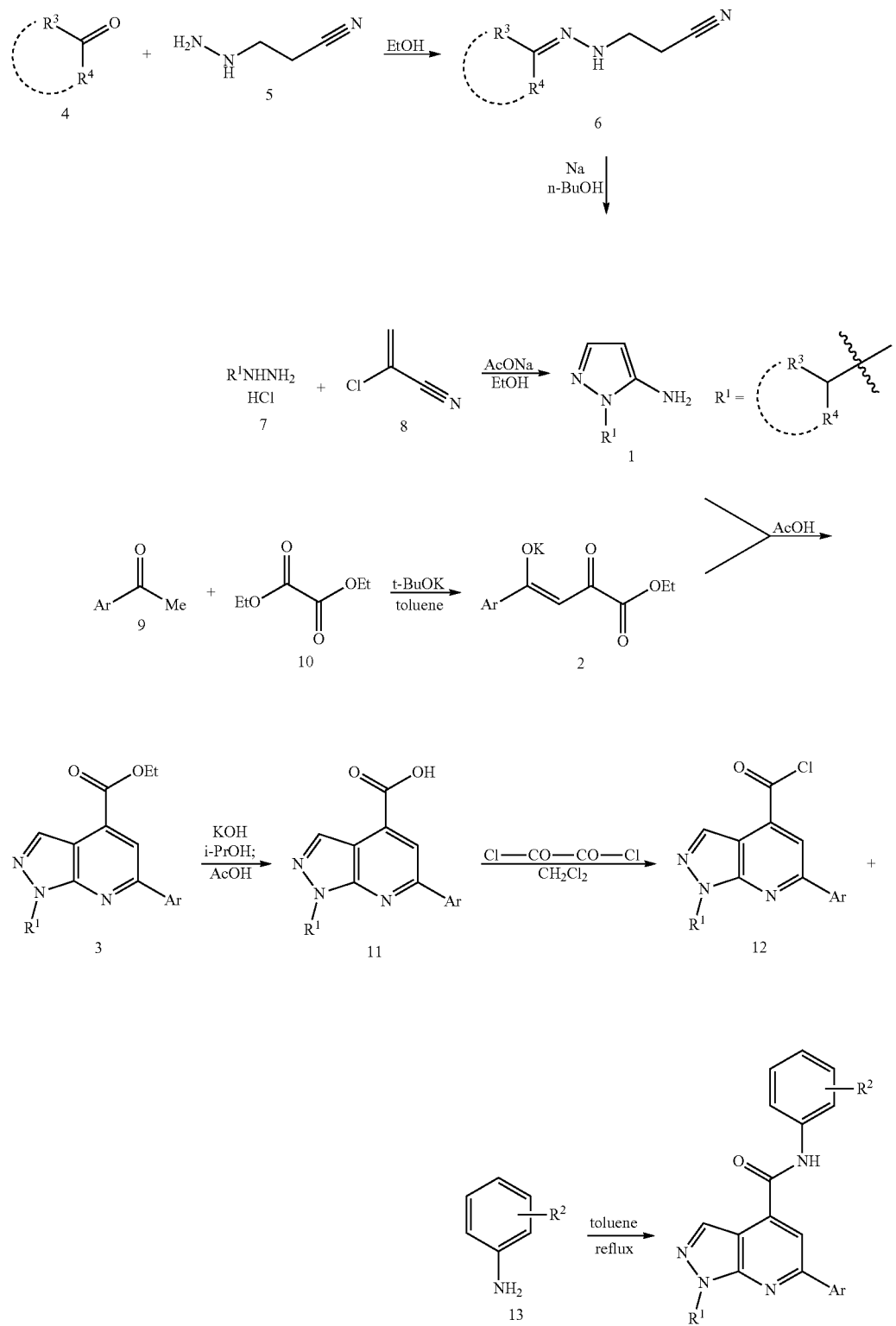

Although this general synthetic route was used for the synthesis of most of the compounds of the present technology presented in Table 1, other methods may be used for specific substitution patterns. The compounds of the present technology were purified by normal synthetic medicinal chemistry procedures, usually column chromatography and their structures were determined by high field NMR spectroscopy.

Biological Testing of Representative Compounds of the Present Technology

Virus Cytopathic Effect Assay:

Cells growing in 96 well plates are infected with a given virus at given low multiplicities of infection pre-determined to result in 100% cytopathic effects (CPE) in the cultures after 3-4 days incubation. Cultures are monitored daily for microscopic signs of typical CPE: rounding of cells and detachment. When CPE appears maximal in the control wells without the antiviral compounds, the cells are fixed with 4% formaldehyde before staining with 0.25% crystal violet solution. Dead cells and debris are washed out and the remaining blue stain intensity in each well is quantified by spectrophotometry at a wavelength of 590 nm ($OD_{590}$) as a measurement of viability.

Drug") of the well are made with the antivirals (Isoprinosine and test compounds). At least 6 concentration points are usually performed. Add 100 μL per well that will be tested for effective concentration ("drug wells") and cytotoxic concentration ("tox wells"). The rabies virus is diluted 1:1000 and 50 μL of this dilution is added per well in the drug wells and virus control wells. Additional media is added to the tox, Control, Virus Control, and Media only wells to ensure the final volume is 200 μL—e.g., tox wells should be 100 μL 2× Drug, 50 μL cells ($5 \times 10^5$ cells/mL), and 50 μL media; Media only wells (row H of Scheme 2) should be 200 μl media. The 96 well plates are then covered and incubated for 5 days at 37° C. in a 5% $CO_2$ atmosphere. Upon completion of the 5-day incubation period, the well plate is visually checked to determine the difference in the Control wells and Virus Control wells as well as any visible toxicity from the compounds. A Promega CellTiter-Glo Luminescent Cell Viability Assay is then performed using the Fluoroskan FL to scan for luminescence.

Scheme 2

|   | 1 | 2 | 3 | 4 | 5 | 6 | 7 | 8 | 9 | 10 | 11 | 12 |
|---|---|---|---|---|---|---|---|---|---|---|---|---|
| A | Drug 1 | Drug 1 | Drug 1 | Drug 1 | Drug 1 | Drug 1 | Drug 2 | Drug 2 | Drug 2 | Drug 2 | Drug 2 | Drug 2 |
| B | 1000 μM | 333 μM | 111 μM | 37 μM | 12.3 μM | 4 μM | 100 μM | 33 μM | 11 μM | 3.7 μM | 1.2 μM | 0.4 μM |
| C |   |   |   |   |   |   |   |   |   |   |   |   |
| D | Cells + 150 μl media (Control) | | | Cells + virus + 100 μl media (Virus control) | | | Cells + 150 μl media (Control) | | | Cells + virus + 100 μl media (Virus control) | | |
| E | Tox 1 | Tox 1 | Tox 1 | Tox 1 | Tox 1 | Tox 1 | Tox 2 | Tox 2 | Tox 2 | Tox 2 | Tox 2 | Tox 2 |
| F | 1000 μM | 333 μM | 111 μM | 37 μM | 12.3 μM | 4 μM | 100 μM | 33.3 μM | 11.1 μM | 3.7 μM | 1.2 μM | 0.4 μM |
| G |   |   |   |   |   |   |   |   |   |   |   |   |
| H | Media only | | | | | | Media only | | | | | |

Drug = 100 μl 2x drug, 50 μl cells (5e5 cells/ml), 50 μl virus (1:1000)
Tox = 100 μl 2x drug, 50 μl cells (5e5 cells/ml), 50 μl media In Vitro Evaluation of Antiviral Activities:

Each compound is initially tested against each virus at 10 μM in a virus CPE assay. A compound that is active against a virus, protecting the cells from CPE, is further evaluated for its 50% effective concentration ($EC_{50}$) value and 50% cytotoxicity concentration ($CC_{50}$) value. Serial 2-fold dilutions of an active compound are prepared. For $EC_{50}$ value determination, a 7-point dose-response curve is constructed using a virus CPE assay and $EC_{50}$ value is estimated using four parameter model or sigmoidal model. For $CC_{50}$ value determination, cells are incubated with serial 2-fold dilutions of a compound for the same period as the virus CPE assay, and then cells were fixed, stained and read as in the virus CPE assay.

Exemplary In Vitro Evaluation of Anti-Rabies Activity:

T-150 flasks of confluent BHK-21 cells are prepared and subsequently trypsinized and made into cell suspensions. 50 μL of a $5 \times 10^5$ cells/mL cell suspension (25,000 cells/well) are loaded into each well of a 96-well, white walled, clear bottom cell culture plate, with the exception of row H which is reserved for Media only (see Scheme 2 below). Concentrations of double the final intended concentration ("2×

Tables 2 and 3 provide the results of evaluating the antiviral activities of certain representative compounds of the present technology with certain enteroviruses. The data in Tables 2 and 3 are $EC_{50}$ values in μM units. Abbreviations are as follows:

CVB3-H3: Coxsackievirus B3-H3

PV1: Poliovirus 1

PV3: Poliovirus 3

CVB1: Coxsackievirus B1

CVB2: Coxsackievirus B2

CVB4: Coxsackievirus B4

CVB5: Coxsackievirus B5

EV71: Enterovirus 71

COX A9: Coxsackievirus A9

ECHO06: Echovirus 6

ECHO07: Echovirus 7

ECHO09: Echovirus 9

ECHO11: Echovirus 11

ECHO25: Echovirus 25

ECHO30: Echovirus 30

TABLE 2

Evaluation of Compounds of the Present Technology Against Enteroviruses

| Compound (JX #) | CVB3-H3 | PV1 | PV3 | CVB1 | CVB2 | CVB4 | CVB5 |
|---|---|---|---|---|---|---|---|
| JX-001 | 1.4 ± 0.6 | 7 ± 0.0 | 7 ± 0.0 | 2.4 ± 0.2 | 2.8 ± 0.4 | 2.3 ± 0.0 | 2.3 ± 0.0 |
| JX-002 | 4.5 ± 1.5 | >25 | >25 | TBD | TBD | TBD | TBD |
| JX-003 | 5.1 ± 0.1 | >25 | >25 | TBD | TBD | TBD | TBD |
| JX-004 | 6.9 ± 0.7 | >25 | >25 | TBD | TBD | TBD | TBD |
| JX-005 | 7.0 ± 2.4 | >25 | >25 | TBD | TBD | TBD | TBD |
| JX-008 | 1.4 ± 0.5 | >25 | >25 | 2.3 ± 0.0 | 2.8 ± 0.4 | 2.3 ± 0.0 | 2.3 ± 0.0 |
| JX-009 | 3.2 ± 0.5 | >25 | >25 | TBD | TBD | TBD | TBD |
| JX-010 | 3.3 ± 1.4 | >25 | >25 | TBD | TBD | TBD | TBD |
| JX-015 | 1.3 ± 0.1 | >25 | >25 | 2.3 | TBD | 3.1 | 2.3 |
| JX-016 | >10 | >10 | >10 | >10 | >10 | >10 | >10 |
| JX-017 | 0.7 ± 0.2 | >25 | >25 | 0.9 ± 0.3 | 1.0 ± 0.3 | 0.8 ± 0.0 | 1.0 ± 0.1 |
| JX-018 | 2.7 ± 0.4 | >25 | >25 | TBD | TBD | TBD | TBD |
| JX-019 | 2.7 ± 0.4 | >25 | >25 | TBD | TBD | TBD | TBD |
| JX-020 | 1.8 ± 0.7 | >25 | >25 | 6 | TBD | 3.1 | 2.3 |
| JX-021 | 1.3 ± 0.2 | >25 | >25 | 2.6 ± 0.5 | 2.6 ± 0.5 | 2.6 ± 0.5 | 2.3 ± 0.0 |
| JX-025 | 0.3 ± 0.0 | 5 ± 0.0 | 5 ± 0.0 | 1.2 ± 0.0 | 1.2 ± 0.0 | 1.1 ± 0.2 | 1.2 ± 0.0 |
| JX-026 | 2.4 ± 0.0 | >25 | >25 | 3.3 | 3.3 | 3.3 | 3.3 |
| JX-030 | 1.3 ± 0.1 | >25 | >25 | 1.6 ± 0.1 | 1.6 ± 0.1 | 2.2 ± 0.1 | 1.2 ± 0.1 |
| JX-033 | 2.6 ± 0.4 | >25 | >25 | 3.9 ± 1.1 | 3.9 ± 1.1 | 3.1 ± 0.1 | 2.7 ± 0.6 |
| JX-038 | 4.7 | >10 | >10 | 4.7 | 4.7 | TBD | TBD |
| JX-039 | 4.7 | >10 | >10 | 4.7 | 4.7 | >10 | >10 |
| JX-040 | 0.6 | >10 | >10 | 0.6 | 0.6 | 0.5 | 0.6 |
| JX-041 | 0.6 | >10 | >10 | 0.6 | 0.6 | 0.6 | 0.6 |
| JX-042 | 0.6 | >10 | >10 | 0.6 | 0.6 | 0.6 | 0.6 |
| JX-043 | 0.6 | >10 | >10 | 0.6 | 0.6 | 0.5 | 0.6 |
| JX-047 | 0.6 | >10 | >10 | 0.6 | 0.6 | 0.6 | 0.6 |
| JX-048 | 1.5 | >10 | >10 | 1.5 | 1.5 | 1.2 | 1.2 |
| JX-052 | 1.2 | >10 | >10 | 1.2 | 1.2 | 1.2 | 1.2 |
| JX-053 | 0.6 | >10 | >10 | 0.6 | 0.6 | 0.6 | 0.6 |
| JX-054 | 4.7 | >10 | >10 | 4.7 | 4.7 | 4.7 | 4.7 |
| JX-056 | 0.6 | 10 | 10 | 0.6 | 0.6 | 0.6 | 0.6 |
| JX-057 | 1.2 | >10 | >10 | 1.2 | 1.2 | 1.2 | 1.2 |
| JX-058 | 1.2 | >10 | >10 | 1.2 | 1.2 | 1.2 | 1.2 |
| JX-059 | 1.2 | >10 | >10 | 1.2 | 1.2 | 1.2 | 1.2 |
| JX-060 | 0.6 | >10 | >10 | 0.6 | 0.6 | 0.6 | 0.6 |
| JX-064 | 0.7 ± 0.1 | 6.25 | 6.25 | 0.6 | 0.6 | 0.6 | 0.6 |
| JX-066 | 0.7 ± 0.2 | >10 | >10 | 0.5 | 0.5 | 0.5 | 0.5 |
| JX-068 | 0.6 | 6.25 | 6.25 | 0.6 | 0.5 | 0.5 | 0.5 |
| JX-069 | 0.6 | >10 | >10 | 0.7 | 0.6 | 0.6 | 0.6 |
| JX-070 | 1.6 ± 0.0 | >10 | >10 | 1.2 | 1.6 | | |
| JX-071 | 4.7 | >10 | >10 | 4.7 | 6.25 | | |
| JX-073 | 0.8 | 5 | 5, 6.3 | 0.6 | 1.2 | | |
| JX-074 | >10 | >10 | >10 | >10 | >10 | >10 | >10 |
| JX-075 | 0.7 ± 0.1 | >10 | >10 | | | | |
| JX-076 | 9.4 ± 0.0 | >10 | >10 | | | | |

1. In Vitro antiviral testing was done in HeLa-RW cells.
2. x.x ± x.x: mean ± standard deviation (sd). $EC_{50}$ values of single experiments are shown as x.x.
3. >10 and >25 entries: compounds were tested in 10 μM or 25 μM, respectively, and no antiviral activities were observed.
4. TBD: A compound is active against an enteroviral infection in 10 μM concentration; $EC_{50}$ not yet determined.
5. A blank cell indicates that the referenced compound has not yet been tested with the indicated enterovirus.

TABLE 3

Evaluation of Compounds of the Present Technology Against Enteroviruses (cont.)

| Compound (JX #) | EV71 | COX A9 | ECHO06 | ECHO07 | ECHO09 | ECHO11 | ECHO25 | ECHO30 |
|---|---|---|---|---|---|---|---|---|
| JX-001 | 1.8 ± 0.5 | 2.6 ± 0.9 | 2.3 ± 0.9 | 2.4 | 2.1 ± 1.2 | 1.5 ± 0.4 | 3 | 1.2 |
| JX-002 | 5.7 ± 1.5 | 5 | 4.4 ± 0.6 | TBD | TBD | 2.9 | TBD | TBD |
| JX-003 | >10 | 7.0 ± 0.8 | 9.2 ± 3.2 | TBD | TBD | 5.3 | TBD | TBD |
| JX-004 | >10 | 6.1 ± 2.2 | 7.8 ± 1.8 | TBD | TBD | 3.8 | TBD | TBD |
| JX-005 | >10 | 7.8 ± 2.6 | 9 | TBD | TBD | 4.5 | TBD | TBD |
| JX-008 | 1.6 ± 0.4 | 2.3 ± 0.8 | 1.9 ± 0.7 | 2.4 | 1.5 ± 1.0 | 1.4 ± 0.4 | 1.5 | 0.8 |
| JX-009 | 3.4 ± 0.7 | 4 | 4.9 ± 0.3 | TBD | TBD | 2.8 | TBD | TBD |
| JX-010 | 3.7 ± 0.2 | 3.1 | 4.2 ± 0.3 | TBD | TBD | 3.2 | TBD | TBD |
| JX-015 | TBD | 1.2 | 1.3 ± 0.1 | TBD | 0.6 | TBD | TBD | TBD |
| JX-017 | 0.9 ± 0.3 | 0.9 ± 0.5 | 1.0 ± 0.4 | 1.3 ± 0.2 | 0.6 | TBD | 1.2 | 0.5 |
| JX-018 | 3.5 | 2.4 | 2.6 ± 0.3 | TBD | TBD | TBD | TBD | TBD |
| JX-019 | 3 | TBD | 2.0 ± 0.6 | TBD | TBD | TBD | TBD | TBD |

TABLE 3-continued

Evaluation of Compounds of the Present Technology Against Enteroviruses (cont.)

| Compound (JX #) | EV71 | COX A9 | ECHO06 | ECHO07 | ECHO09 | ECHO11 | ECHO25 | ECHO30 |
|---|---|---|---|---|---|---|---|---|
| JX-020 | 3 | 2.4 | 2.4 ± 0.0 | TBD | TBD | TBD | TBD | TBD |
| JX-021 | 2.4 ± 0.8 | 1.6 | 1.5 ± 0.5 | 2.9 | 1.2 | TBD | TBD | TBD |
| JX-025 | 1.3 ± 0.1 | 2.1 ± 0.7 | 1.1 ± 0.3 | 2.1 ± 0.6 | 1.2 | TBD | 1.1 | 0.6 |
| JX-026 | 2.6 ± 0.3 | TBD | 2.4 | TBD | TBD | TBD | TBD | TBD |
| JX-030 | 1.4 ± 0.2 | 1.7 ± 0.1 | 1.2 ± 0.1 | 2.6 ± 0.1 | 1.9 | TBD | 0.9 | 0.6 |
| JX-033 | 2.5 ± 0.7 | 2.4 | 2.4 | | | | | |
| JX-038 | 3.2 ± 0.1 | 3 | 3.9 | TBD | TBD | TBD | TBD | TBD |
| JX-039 | 3.2 ± 0.1 | 4.5 | 2.4 | >10 | >10 | >10 | >10 | >10 |
| JX-040 | 0.5 ± 0.1 | 0.6 | 0.4 | 0.6 | | 0.5 | 0.6 | <0.4 |
| JX-041 | 0.5 ± 0.1 | 0.6 | 0.4 | 0.7 | | 0.6 | 0.6 | <0.4 |
| JX-042 | 0.4 ± 0.0 | 0.5 | 0.2 | | | | | |
| JX-043 | 0.5 ± 0.1 | 0.5 | 0.2 | | 0.7 | | | |
| JX-046 | >10 | >10 | >10 | >10 | >10 | >10 | >10 | 6.25 |
| JX-047 | 0.5 ± 0.1 | 0.5 | 0.3 | 0.8 | | | | |
| JX-048 | 1.3 ± 0.2 | 1.2 | 1.1 | | | | | |
| JX-052 | 0.8 ± 0.1 | 0.8 | | 0.78 | 0.2 | 0.6 | | 0.4 |
| JX-053 | 0.7 ± 0.1 | 0.8 | | 0.45 | 0.2 | 0.6 | | 0.6 |
| JX-054 | 4 | 4.7 | | 4.7 | 2.4 | 3.1 | | 4.7 |
| JX-056 | 0.5 ± 0.1 | 0.6 | | 0.45 | 0.2 | 0.2 | | 0.3 |
| JX-057 | 0.8 | | | | 0.4 | 1.2 | | |
| JX-058 | 1.2 | | | | 0.6 | 1.3 | | |
| JX-059 | 0.8 | | | | 0.4 | 1.2 | | |
| JX-060 | 2.4 | TBD | TBD | TBD | TBD | TBD | TBD | TBD |
| JX-061 | TBD | TBD | TBD | TBD | TBD | TBD | TBD | TBD |
| JX-064 | 0.5 | 0.6 | | | 0.2 | | | |
| JX-066 | 0.4 | 0.4 | | | 0.2 | | | |
| JX-067 | TBD | TBD | TBD | TBD | TBD | TBD | TBD | TBD |
| JX-068 | 0.5 | 0.6 | | | 0.2 | | | |
| JX-069 | 0.8 | 1.3 | | | 0.3 | | | |
| JX-070 | 0.7 | | | 2.3 | | | | |
| JX-071 | 4.7 | | | 9.4 | | | | |
| JX-073 | 0.5 | | | 1.2 | | | | |
| JX-074 | >10 | >10 | >10 | >10 | >10 | >10 | >10 | >10 |
| JX-075 | 1.2 | | | | | | | |
| JX-076 | 12.5 | | | | | | | |

1. In Vitro antiviral testing was done in LLC cells.
2. x.x ± x.x: mean ± standard deviation (sd). $EC_{50}$ values of single experiments are shown as x.x.
3. >10 and >25 entries: compounds were tested in 10 μM or 25 μM, respectively, and no antiviral activities were observed.
4. TBD: A compound is active against an enteroviral infection in 10 μM concentration; $EC_{50}$ not yet determined.
5. A blank cell indicates that the referenced compound has not yet been tested with the indicated enterovirus.

Table 4 provides the compound concentration in M units that reduces cell viability of the host cell by 50% ($CC_{50}$) for certain compounds of the present technology for HeLa-RW and LLC cells. Blank cells indicate that the cytotoxicity assessment is not yet complete. Such data allows for calculation of the selectivity index ($SI_{50}=CC_{50}/EC_{50}$) of each compound for each virus and strain in a cell line.

TABLE 4

Evaluation of $CC_{50}$ of Compounds of the Present Technology

| Compound (JX #) | HeLa-RW | LLC |
|---|---|---|
| JX-001 | 12.5 | 50 |
| JX-002 | 37.5 | >200 |
| JX-003 | 37.5 | 45 |
| JX-004 | >200 | 100 |
| JX-005 | 37.5 | 50 |
| JX-008 | >200 | >200 |
| JX-009 | >200 | >200 |
| JX-010 | >200 | 100 |
| JX-015 | >200 | >200 |
| JX-017 | >200 | >200 |
| JX-018 | >200 | 100 |
| JX-019 | >200 | 75 |
| JX-020 | >200 | >200 |
| JX-021 | >200 | >200 |
| JX-025 | 50 | 25 |
| JX-026 | >200 | >200 |
| JX-030 | 25 | >100 |
| JX-033 | 10 | 25 |
| JX-038 | 10 | 12.5 |
| JX-039 | 10 | |
| JX-040 | >200 | >200 |
| JX-041 | 37.5 | 75 |
| JX-042 | 6 | 6.25 |
| JX-043 | 20 | 50 |
| JX-046 | | 20 |
| JX-047 | 200 | 50 |
| JX-048 | 20 | >200 |
| JX-052 | 12 | >200 |
| JX-053 | 12 | 25 |
| JX-054 | 12 | 50 |
| JX-056 | 25 | >200 |
| JX-057 | 18 | 25 |
| JX-058 | 40 | 50 |
| JX-059 | >200 | >200 |
| JX-060 | 18 | 37 |
| JX-064 | 18 | 20 |
| JX-066 | 18 | 20 |
| JX-067 | 18 | |
| JX-068 | 18 | 25 |

TABLE 4-continued

Evaluation of CC$_{50}$ of Compounds of the Present Technology

| Compound (JX #) | HeLa-RW | LLC |
|---|---|---|
| JX-069 | >200 | 50 |
| JX-070 | 18.8 | 12.5 |
| JX-071 | 25 | 25 |
| JX-073 | 18.8 | 25 |
| JX-074 | | |
| JX-075 | 37.5 | >200 |
| JX-076 | 37.5 | 50 |

Thus, comparing Tables 2-3 with Table 4 allows for determination of the SI$_{50}$ of the compounds for each tested virus in addition to the activity. For example, not only does JX-040 possess a lower EC$_{50}$ value for CVB3-H3 (Coxsackievirus B3-H3) as compared to JX-001, the SI$_{50}$ for JX-040 surprisingly exceeds 250 (>200/0.8) for CVB3-H3 while the SI$_{50}$ for JX-001 is about 8 (12.5/1.4) for CVB3-H3.

Table 5 provides the results of cell-based assays with RD cells evaluating the antiviral activities of certain representative compounds of the present technology with certain strains of Enterovirus D68, namely strains Fermon ("D68/Fermon"), US/Mo/14-18949 ("D68/US/Mo/14-18949"), and US/KY/14-18953 ("D68/US/KY/14-18953"). The values indicated in the strain columns are EC$_{50}$ values in μM units. The CC$_{50}$ values (in μM units) for RD cells are also provided for evaluation of SI$_{50}$.

TABLE 5

Evaluation of Activities of Compounds of the Present Technology Against strains of Enterovirus D68

| Compound (JX #) | Fermon | US/Mo/14-18949 | US/KY/14-18953 | CC$_{50}$ (RD) |
|---|---|---|---|---|
| JX-001 | 0.35 ± 0.05 | 0.33 ± 0.05 | 0.50 ± 0.17 | 200 |
| JX-007 | 0.80 ± 0.28 | 0.66 ± 0.10 | 1.20 ± 0.00 | >200 |
| JX-008 | 0.33 ± 0.06 | 0.28 ± 0.08 | 0.40 ± 0.17 | 100 |
| JX-013 | 1.33 ± 0.23 | 1.07 ± 0.23 | 1.80 ± 0.44 | >200 |
| JX-017 | 0.33 ± 0.06 | 0.35 ± 0.06 | 0.50 ± 0.17 | >200 |
| JX-025 | 0.1, 0.1, 0.15 | 0.06 ± 0.02 | 0.15 ± 0.00 | 50 |
| JX-026 | 1.2 ± 0.0 | 1.0 ± 0.02 | 1.3 ± 0.2 | >200 |
| JX-030 | | 0.3 | 0.6 | 25 |

TABLE 5-continued

Evaluation of Activities of Compounds of the Present Technology Against strains of Enterovirus D68

| Compound (JX #) | Fermon | US/Mo/14-18949 | US/KY/14-18953 | CC$_{50}$ (RD) |
|---|---|---|---|---|
| JX-037 | 0.86 ± 0.31 | 0.57 ± 0.15 | 1.1 ± 0.3 | >200 |
| JX-040 | 0.25 ± 0.09 | 0.17 ± 0.03 | 0.27 ± 0.06 | >200 |
| JX-047 | 0.30 ± 0.00 | 0.16 ± 0.04 | 0.30 ± 0.00 | 75 |
| JX-048 | 2.8 ± 0.45 | 2.1 ± 0.6 | 4.1 ± 1.2 | >200 |
| JX-052 | 0.57 ± 0.25 | 0.31 ± 0.07 | 0.53 ± 0.29 | >200 |
| JX-054 | 2.40 ± 0.00 | 2.53 ± 0.23 | 3.40 ± 1.18 | 50 |
| JX-055 | 0.70 ± 0.20 | 0.40 ± 0.20 | 0.73 ± 0.12 | >200 |
| JX-056 | <0.1 | <0.1 | 0.12 | 25 |
| JX-059 | 0.69 ± 0.09 | 0.57 ± 0.22 | 0.87 ± 0.31 | 75 |
| JX-062 | 0.16 ± 0.03 | 0.13 ± 0.03 | 0.26 ± 0.07 | 25 |
| JX-064 | | 0.05 | 0.17 | 25 |
| JX-065 | 6.30 ± 0.00 | 4.70 ± 1.60 | 6.30 ± 0.00 | 75 |
| JX-066 | 0.06 ± 0.02 | 0.05 ± 0.01 | 0.15 ± 0.00 | 25 |
| JX-067 | 1.60 ± 0.00 | 1.27 ± 0.12 | 2.27 ± 0.23 | 100 |
| JX-068 | 0.05 ± 0.00 | 0.05 ± 0.01 | 0.11 ± 0.01 | 25 |
| JX-069 | | 0.05 | 0.15 | 25 |
| JX-070 | 0.35 | | 0.7 | 12.5 |
| JX-071 | 1.2 | | 2.3 | 37 |
| JX-072 | <0.4 | | 0.6 | 25 |
| JX-073 | <0.4 | | <0.4 | 25 |
| JX-075 | <0.4 | <0.4 | <0.4 | 25 |
| JX-076 | 4 | 4 | 4.7 | 45 |

1. In Vitro antiviral testing was done in RD cells.
2. x.x ± x.x: mean ± standard deviation (sd). EC$_{50}$ values of single experiments are shown as x.x. EC$_{50}$ values of a few experiments are listed out as a series of values.
3. A blank cell indicates that the referenced compound has not yet been tested with the indicated Enterovirus D68 strain.

This data illustrates that the compounds of the present technology have high activity against these strains with concurrently exhibiting excellent SI values. For example, JX-001, JX-008, JX-017, JX-025, JX-026, JX-030, JX-037, JX-040, JX-047, JX-048, JX-52, JX-055, JX-059, JX-062, JX-066, JX-067, and JX-068 each have at least one strain against which the compound has an EC$_{50}$ less than 1 μM while concurrently having a SI greater than 25. As a further example, for the 2014 epidemic strain of Enterovirus D68/US/Mo/14-18949, JX-040 has an SI of over 1,200 (>200/0.17=>1,200).

Table 6 provides the results of cell-based assays evaluating the antiviral activities of certain representative compounds of the present technology with certain paramyxoviruses, respiratory viruses, flaviviridae viruses, bunyaviridae viruses, and togaviridae viruses, and rabies virus. EC$_{50}$ values and CC$_{50}$ values are each in μM units.

TABLE 6

| Virus Family/Type | Cell Culture | Results | Positive Control | JX001 | JX008 | JX017 | JX025 | JX030 |
|---|---|---|---|---|---|---|---|---|
| Paramyxovirus | | | | | | | | |
| Measles | Vero 76 | EC$_{50}$ | 2.4 (3-Deazaguanine) | >4 | 34 | 8.9 | 7.1 | 20.5 |
| CC | Vero 76 | CC$_{50}$ | >100 | 4 | >100 | 22 | 18 | >100 |
| | Vero 76 | SI$_{50}$ | >42 | 0 | >2.9 | 2.5 | 2.5 | >4.9 |
| Respiratory viruses | | | | | | | | |
| SARS Coronavirus | Vero 76 | EC$_{50}$ | 0.19 (M128533) | 3.2 | 68 | >10 | >7.2 | 4.4 |
| Urbani | Vero 76 | CC$_{50}$ | >10 | 3.3 | >100 | 10 | 7.2 | 18.7 |
| | Vero 76 | SI$_{50}$ | >53 | 1 | >1.5 | 0 | 0 | 4.2 |
| Influenza A H1N1 | MDCK | EC$_{50}$ | 7.5 (Ribavirin) | >100 | 70 | >100 | >100 | 10.7 |
| California/07/2009 | MDCK | CC$_{50}$ | >320 | >100 | >100 | >100 | >100 | 17.7 |
| | MDCK | SI$_{50}$ | >43 | 0 | >1.4 | 0 | 0 | 1.7 |
| RSV (resp syncitial virus) | MA-104 | EC$_{50}$ | 12 (Ribavirin) | 3.4 | >100 | 69 | >100 | 7.0 |
| A2 | MA-104 | CC$_{50}$ | 250 | 4.7 | >100 | >100 | >100 | 67.6 |
| | MA-104 | SI$_{50}$ | 21 | 1.4 | 0 | >1.4 | 0 | 9.6 |
| Flaviviridae | | | | | | | | |
| Japanese Encephalitis | Vero 76 | EC$_{50}$ | 0.00003 (Infergen) | >0.014 | >0.44 | >0.43 | 0.31 | 3.4 |
| SA-14 | Vero 76 | CC$_{50}$ | >0.01 | 0.014 | 0.44 | 0.43 | 1.3 | 8.1 |
| | Vero 76 | SI$_{50}$ | >330 | 0 | 0 | 0 | 4.2 | 2.4 |

TABLE 6-continued

| Virus Family/Type | Cell Culture | Results | Positive Control | JX001 | JX008 | JX017 | JX025 | JX030 |
|---|---|---|---|---|---|---|---|---|
| Powassan | BHK | $EC_{50}$ | 0.00026 (Infergen) | >33 | >38 | 32 | >8.9 | >85.8 |
| LB | BHK | $CC_{50}$ | >0.01 | >33 | 38 | 37 | 8.9 | >85.8 |
|  | BHK | $SI_{50}$ | >38 | 0 | 0 | 1.2 | 0 | 0 |
| Yellow Fever Virus | Vero | $EC_{50}$ | 0.29 (6-Azauridine) | >4.8 | 45 | >9.9 | >4.8 | >11.1 |
| 17D | Vero | $CC_{50}$ | 10 | 4.8 | 50 | 9.9 | 4.8 | 11.1 |
|  | Vero | $SI_{50}$ | 34 | 0 | 1.1 | 0 | 0 | 0 |
| Bunyaviridae ||||||||| 
| Punta Toro virus | Vero 76 | $EC_{50}$ | 11 (Ribavirin) | >39 | 23 | 12 | 38 | >78 |
| Adames | Vero 76 | $CC_{50}$ | >1000 | 39 | >100 | 30 | >100 | 78 |
|  | Vero 76 | $SI_{50}$ | >91 | 0 | >4.3 | 2.5 | >2.6 | 0 |
| Rift Valley virus | Vero 76 | EC50 | 9.1 (Ribavirin) | >50 | >77 | >52 | >100 | 140.4 |
| MP-12 | Vero 76 | CC50 | >1000 | 50 | 77 | 52 | >100 | 169 |
|  | Vero 76 | SI50 | >110 | 0 | 0 | 0 | 0 | 1.2 |
| Togaviridae ||||||||| 
| Venezuelan Encephalitis | Vero 76 | $EC_{50}$ | 0.000016 (Infergen) | >0.98 | >0.48 | 0.32 | >0.88 | >9.4 |
| TC-83 | Vero 76 | $CC_{50}$ | >0.01 | 0.98 | 0.48 | 0.36 | 0.88 | 9.4 |
|  | Vero 76 | $SI_{50}$ | >630 | 0 | 0 | 1.1 | 0 | 0 |
| Chikungunya | Vero 76 | $EC_{50}$ | 0.00014 (Infergen) | 0.31 | >0.66 | 0.29 | 0.3 | >1.3 |
| S-27 (VR-64) | Vero 76 | $CC_{50}$ | >0.01 | 0.36 | 0.66 | 0.36 | 0.33 | 1.3 |
|  | Vero 76 | $SI_{50}$ | >71 | 1.2 | 0 | 1.2 | 1.1 | 0 |
| Miscellaneous ||||||||| 
| Rabies | BHK-21 | EC50 | 134.10 (Isoprinosine) | >100 | >100 | >100 | >12.18 | 88.4 |
| Flury | BHK-21 | CC50 | >1000 | >100 | >100 | >100 | 12.18 | >260 |
|  | BHK-21 | SI50 | >7 | 1 | 1 | 1 | 0 | >2.9 |

$EC_{50}$: compound concentration that reduces viral replication by 50%
$CC_{50}$: compound concentration that reduces cell viability by 50%
$SI_{50}$: selectivity index ($CC_{50}/EC_{50}$)

Exemplary Pharmacokinetic Studies

Analysis of Pharmacokinetics and Acute Toxicity in Mice:

BALB/c mice (weight, 15 to 20 g), will be obtained, weighed, and placed in cages in groups of 4 or 5. A single intravenous dose of the test compound (e.g., 20 milligrams/gram of body weight) will be administered to each animal via tail vein or retroorbital injection. At distributed time points after injection (e.g., 15, 30, 60 minutes, and 2, 4, 6, 8, and 12 hours), small volumes of blood will be collected from the tail veins or retroorbital plexus of each animal. Serum concentrations of the test compound will be determined by high pressure liquid chromatography or similar method. Standard computational methods will be used to estimate typical pharmacokinetic parameters for each compound, including the volume of distribution, time to peak concentration, maximum concentration, area under the concentration curve, and minimum compound concentration. These values will be computed for each mouse and geometric mean values for each parameter will be determined for the group of animals. Based on this initial analysis, a dose and dosing interval will be selected to maintain serum concentrations shown in in vitro experiments to inhibit replication of the particular virus.

The tolerability of this projected dose will be determined by providing dosages of the test compound for 7 days. Weights, feeding, and grooming behavior will be recorded daily. After 7 days, animals will be euthanized and blood will be collected for examination of standard white blood cell, platelet, and hematocrit measurement, as well as quantitation of serum parameters of hepatic, renal, and pancreatic injury and function. Animals will undergo necropsy and tissue specimens will be submitted for standard histological examination of liver, heart, pancreas, and other organs. Maintenance of pretreatment weight (or loss of no more than 10% of weight over 7 days), and maintaining all laboratory parameters in the normal range without marked organ changes will be considered to be indicative of tolerance of the compound tested.

Exemplary Mouse Studies of Inhibition of Viruses

Compound Preparation and Dosing:

Compounds will be formulated with an appropriate vehicle for the study, such as a suspension in a 0.5% xanthan gum-1% Tween 80 vehicle. The compound will be administered intragastrically with a 0.5-ml Glaspak syringe fitted with a 24-gauge feeding needle (Popper and Sons, Inc., New York, N.Y.).

Infection of Suckling Mice:

Newborn mouse pups of both sexes (weight, 1.2 to 1.9 g), born within 24 h of receipt, will obtained with their dams. The pups will be pooled, weighed, and distributed to the nursing dams in groups of 10. Three cages (30 pups) will be included for each dosage group. Each mouse pup will infected subcutaneously over the right shoulder within 24 h of birth with the virus. The amount of virus inoculated will be titrated to produce approximately 80% mortality in untreated animals over a 14-day observation period. The compound of interest will be administered as a single, 0.03-ml dose 1 day postinfection. Mouse pups will be checked daily for evidence of paralysis or death (animals that are in severe distress or paralyzed will be killed). It is expected that a suitable dosage of compounds of the present technology will be determined that will allow at least eighty percent of treated virus-infected animals to survive the entire 14-day observation period. Separate groups of animals will be euthanized at 7 days to determine if the amount of virus detected in homogenates of the liver, heart, spleen and brain by quantitative viral culture or reverse transcriptase polymerase chain reaction (PCR) is significantly reduced by the daily administration of the test compound. Non-parametric statistical tests such as the Wilcoxon-Rank Sum Test will be used to determine if a significant reduction in the amount of virus is present. Greater than a ten-fold change in the amount of virus is generally required to be considered significant Infection of Adult Mice:

Adult mice will be housed 4 or 5 to a cage. Each mouse will infected by intraperitoneal injection with the test virus, or a suitable control treatment, such as a substance used to dissolve a compound of the present technology. The amount of virus inoculated will be titrated to produce approximately 80% mortality in untreated animals over the 14 day observation period. The compound of interest will be administered at a frequency and dosage estimated from the pharmacokinetic analysis discussed previously. Animals will be examined for evidence of disease or death (animals that are in severe distress or paralyzed will be killed). It is expected that a suitable dosage of compounds of the present technology will be determined that will allow at least eighty percent of treated virus-infected animals to survive the entire 14-day observation period. Separate groups of animals will be euthanized at 7 days to determine if the amount of virus detected in homogenates of the liver, heart, spleen and brain is significantly reduced by the daily administration of the test compound. Non-parametric statistical tests such as the Wilcoxon-Rank Sum Test will be used to determine if a significant reduction in the amount of virus is present, as well as a reduction in the mortality rates of groups of animals receiving both the test compounds and viral infection, compared to animals receiving either the compound or the virus alone.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such A. A compound according to Formula I:

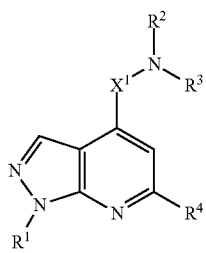

(I)

or a pharmaceutically acceptable salt thereof, wherein
$R^1$ is H, alkyl, cycloalkyl, heterocyclyl, aryl, or heteroaryl;
$R^2$ is a substituted or unsubstituted aryl or a substituted or unsubstituted heteroaryl;
$R^3$ is H or $C_1$-$C_6$ alkyl;
or —N($R^2$)($R^3$) is a substituted or unsubstituted aryl-fused non-aromatic heterocyclyl group or a substituted or unsubstituted heteroaryl-fused non-aromatic heterocyclyl group, preferably where —N($R^2$)($R^3$) is a substituted or unsubstituted indolin-1yl group or a substituted or unsubstituted 2,3-dihydro-1H-pyrrolo[2,3-b]pyridin-1-yl group;
$R^4$ is a substituted or unsubstituted cycloalkyl, aryl, or heteroaryl; and
$X^1$ is —C(O)—, —C(NH)—, —C(S)—, or —S(O)$_2$—.

B. The compound of Paragraph A, wherein:
$R^1$ is H, alkyl, cycloalkyl, or aryl;
$R^2$ is a substituted or unsubstituted heteroaryl group or a substituted aryl group where the substituents of the aryl group are selected from halogen, nitro, alkanoyl, carbamoyl, ester, amido, sulfone, sulfonyl, sulfonamido, or trifluoromethyl;
$R^3$ is H, or —N($R^2$)($R^3$) is a substituted or unsubstituted indolinyl group;
provided that where $R^1$ is isopropyl, $R^3$ is hydrogen, $R^4$ is 2-thiophenyl, and $X^1$ is —C(O)—, $R^2$ is not 2-fluorophenyl or 2-chloro-4-fluorophenyl.

C. The compound of Paragraph A or Paragraph B, wherein $R^1$ is $C_1$-$C_6$ alkyl, $C_4$-$C_7$ cycloalkyl, or phenyl group.

D. The compound of any one of Paragraphs A-C, wherein $R^1$ is $C_1$-$C_6$ alkyl, unsubstituted $C_4$-$C_7$ cycloalkyl, or substituted phenyl.

E. The compound of any one of Paragraphs A-D, wherein $R^2$ is a substituted or unsubstituted heteroaryl group or a substituted aryl group where the aryl group bears 1, 2, or 3 substituents.

F. The compound of any one of Paragraphs A-E, wherein $R^2$ is an unsubstituted six-membered nitrogen-containing heteroaryl group or a substituted phenyl group where the substituents of the phenyl group are selected from halogen, amido, sulfonyl, sulfonamido, and trifluoromethyl.

G. A compound according to Formula II:

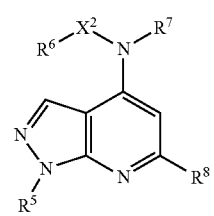

or a pharmaceutically acceptable salt thereof;
wherein
$R^5$ is H, alkyl, cycloalkyl, or aryl;
$R^6$ is aryl, heteroaryl, or aryloyl;
$R^7$ is H, aryl, heteroaryl, or aryloyl;
$R^8$ is cycloalkyl, phenyl, or heteroaryl; and
$X^2$ is —C(O)—, —C(NH)—, —C(S)—, or —S(O)$_2$—.

H. A compound according to Formula III:

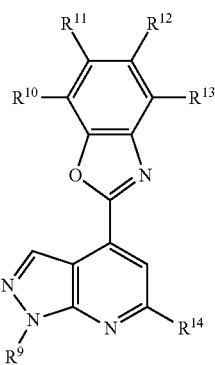

or a pharmaceutically acceptable salt thereof;

wherein
R$^9$ is H, alkyl, cycloalkyl, or aryl;
R$^{10}$, R$^{11}$, R$^{12}$, and R$^{13}$ are each independently H, halogen, nitro, alkanoyl, carbamoyl, ester, amido, sulfone, sulfonyl, sulfonamido, or trifluoromethyl; and
R$^{14}$ is cycloalkyl, phenyl, or heteroaryl.

I. The compound of any one of Paragraphs A-H, wherein the compound is selected from the compounds of Table 1 with the exception of JX-001.

J. The compound of any one of Paragraphs A-I, wherein the compound is JX-008, JX-017, JX-025, JX-026, JX-030, JX-037, JX-040, JX-041, JX-043, JX-047, JX-048, JX-52, JX-055, JX-056, JX-059, JX-062, JX-066, JX-067, or JX-068 of Table 1.

K. A composition comprising a compound of any one of Paragraphs A-J and a pharmaceutically acceptable carrier.

L. A pharmaceutical composition for treating an enterovirus, paramyxovirus, respiratory virus, flaviviridae virus, bunyaviridae virus, togaviridae virus, or rabies virus infection, the composition comprising an effective amount of the compound of any one of Paragraphs A-J and a pharmaceutically acceptable excipient.

M. The pharmaceutical composition of Paragraph L, wherein the pharmaceutical composition is packaged in unit dosage form.

N. A method for inhibiting the replication of an enterovirus, paramyxovirus, respiratory virus, flaviviridae virus, bunyaviridae virus, togaviridae virus, or rabies virus in a cell infected with the enterovirus, paramyxovirus, respiratory virus, flaviviridae virus, bunyaviridae virus, togaviridae virus, or rabies virus in a cell, the method comprising contacting the cell with a compound of any one of Paragraphs A-J.

O. The method of Paragraph N, wherein the method comprises contacting the cell with an effective amount of the compound.

P. The method of Paragraph N or Paragraph O, wherein the enterovirus is Coxsackievirus A9, Coxsackievirus A16, Coxsackievirus B1, Coxsackievirus B2, Coxsackievirus B3-H3, Coxsackievirus B4, Coxsackievirus B5, Enterovirus 68, Enterovirus 71, Echovirus 6, Echovirus 7, Echovirus 9, Echovirus 11, Echovirus 18, Echovirus 25, Echovirus 30, Poliovirus 1, or Poliovirus 3.

Q. The method of any one of Paragraphs N-P, wherein the paramyxovirus is measles.

R. The method of any one of Paragraphs N-Q, wherein the respiratory virus is SARS coronavirus, influenza A H1N1, or respiratory syncytial virus.

S. The method of any one of Paragraphs N-R, wherein the flaviviridae virus is Japanese encephalitis, Powassan virus, or Yellow Fever virus.

T. The method of any one of Paragraphs N-S, wherein the bunyaviridae virus is Punta Toro virus or Rift Valley virus.

U. The method of any one of Paragraphs N-T, wherein the togaviridae virus is Venezuelan encephalitis virus or chikungunya virus.

V. A method of inhibiting death of a cell infected with an enterovirus, paramyxovirus, respiratory virus, flaviviridae virus, bunyaviridae virus, togaviridae virus, or rabies virus, the method comprising contacting the cell with an effective amount of a compound of any one of Paragraphs A-J.

W. The method of Paragraph V, wherein the method comprises contacting the cell with an effective amount of the compound.

X. The method of Paragraph V or Paragraph W, wherein the enterovirus is Coxsackievirus A9, Coxsackievirus A16, Coxsackievirus B1, Coxsackievirus B2, Coxsackievirus B3-H3, Coxsackievirus B4, Coxsackievirus B5, Enterovirus 68, Enterovirus 71, Echovirus 6, Echovirus 7, Echovirus 9, Echovirus 11, Echovirus 18, Echovirus 25, Echovirus 30, Poliovirus 1, or Poliovirus 3.

Y. The method of any one of Paragraphs V-X, wherein the paramyxovirus is measles.

Z. The method of any one of Paragraphs V-Y, wherein the respiratory virus is SARS coronavirus, influenza A H1N1, or respiratory syncytial virus.

AA. The method of any one of Paragraphs V-Z, wherein the flaviviridae virus is Japanese encephalitis, Powassan virus, or Yellow Fever virus.

AB. The method of any one of Paragraphs V-AA, wherein the bunyaviridae virus is Punta Toro virus or Rift Valley virus.

AC. The method of any one of Paragraphs V-AB, wherein the togaviridae virus is Venezuelan encephalitis virus or chikungunya virus.

AD. A method of treating a patient or animal infected with an enterovirus, paramyxovirus, respiratory virus, flaviviridae virus, bunyaviridae virus, togaviridae virus, or rabies virus, the method comprising administration of a compound of any one of Paragraphs A-J to the patient or animal.

AE. The method of Paragraph AD, wherein the method comprises administration of an effective amount of the compound to the patient or animal.

AF. The method of Paragraph AD or Paragraph AE, wherein administration of the compound to the patient or animal treats the patient or animal infected with the enterovirus, paramyxovirus, respiratory virus, flaviviridae virus, bunyaviridae virus, togaviridae virus, or rabies virus.

AG. The method of any one of Paragraphs AD-AF, wherein the enterovirus is Coxsackievirus A9, Coxsackievirus A16, Coxsackievirus B1, Coxsackievirus B2, Coxsackievirus B3-H3, Coxsackievirus B4, Coxsackievirus B5, Enterovirus 68, Enterovirus 71, Echovirus 6, Echovirus 7, Echovirus 9, Echovirus 11, Echovirus 18, Echovirus 25, Echovirus 30, Poliovirus 1, or Poliovirus 3.

AH. The method of any one of Paragraphs AD-AG, wherein the paramyxovirus is measles.

AI. The method of any one of Paragraphs AD-AH, wherein the respiratory virus is SARS coronavirus, influenza A H1N1, or respiratory syncytial virus.

AJ. The method of any one of Paragraphs AD-AI, wherein the flaviviridae virus is Japanese encephalitis, Powassan virus, or Yellow Fever virus.

AK. The method of any one of Paragraphs AD-AJ, wherein the bunyaviridae virus is Punta Toro virus or Rift Valley virus.

AL. The method of any one of Paragraphs AD-AK, wherein the togaviridae virus is Venezuelan encephalitis virus or chikungunya virus.

AM. The method of any one of Paragraphs AD-AL, wherein the administration comprises oral administration, parenteral administration, or nasal administration.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

REFERENCES

1. Cherry, J. D., Krogstad P. K., *Enteroviruses and Parechoviruses*, in *Textbook of Pediatric Infectious Diseases*, R. D. Feigin, et al., Editors. 2009, WB Saunders Co: Philadelphia, Pa., 1984-2041.
2. a) McMinn, P. et al. (2001) *Neurological manifestations of enterovirus 71 infection in children during an outbreak of hand, foot, and mouth disease in Western Australia.* Clin Infect Dis. 32(2):236-242. b) McMinn, P. C. (2002) *An overview of the evolution of enterovirus 71 and its clinical and public health significance.* FEMS Microbiol Rev. 26(1):91-107.
3. Seiff, A. (2012) *Cambodia unravels cause of mystery illness.* Lancet. 380(9838):206.
4. a) Verma, N. A. et al. (2009) *Outbreak of life-threatening coxsackievirus B1 myocarditis in neonates.* Clin Infect Dis. 49(5):759-763. b) Wikswo, M. E. et al. (2009) *Increased activity of Coxsackievirus B1 strains associated with severe disease among young infants in the United States, 2007-2008.* Clin Infect Dis. 49(5):-e51.
5. a) *Notes from the field: severe hand, foot, and mouth disease associated with coxsackievirus A6—Alabama, Connecticut, California, and Nevada, November 2011-February 2012.* MMWR Morb Mortal Wkly Rep, 2012. 61(12): p. 213-4. b) Flett, K. et al. (2012) *Hand, foot, and mouth disease caused by coxsackievirus a6.* Emerg Infect Dis. 18(10): 1702-1704. c) Mathes, E. F. et al. (2013) *"Eczema Coxsackium" and Unusual Cutaneous Findings in an Enterovirus Outbreak.* Pediatrics.
6. a) *Nonpolio enterovirus and human parechovirus surveillance - - - United States, 2006-2008.* MMWR Morb Mortal Wkly Rep, 2010. 59(48):1577-1580. b) *Progress toward interruption of wild poliovirus transmission—worldwide, January 2011-March 2012.* MMWR Morb Mortal Wkly Rep, 2012. 61:353-357. c) De Palma, A. M. et al. (2008) *Selective inhibitors of picornavirus replication.* Med Res Rev. 28(6):823-884.
7. Pamukcu, R.; Piazza, G. A. U.S. Pat. No. 5,942,520, 24 Aug. 1999.
8. a) MacKy, M. et al. (2015) *Gas-Phase Synthesis of Pyrazolo[3,4-b]pyridin-4-ones.* Synthesis 47(2):242-248. b) Ji, N. et al. (2010) *Synthesis of 1-substituted-3-aminopyrazoles.* Tetrahedron Letters 51(52):6799-6801.
9. Chen, H. et al. (2014) *Discovery of a novel pyrazole series of group X secreted phospholipase A2 inhibitor (sPLA2X) via fragment based virtual screening.* Bioorganic & Medicinal Chemistry Letters 24(22):5251-5255.

What is claimed is:
1. A compound according to Formula I:

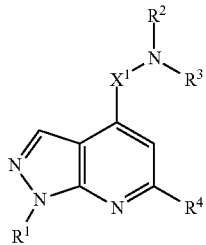

or a pharmaceutically acceptable salt thereof;
wherein:
R¹ is isopropyl;
R² is

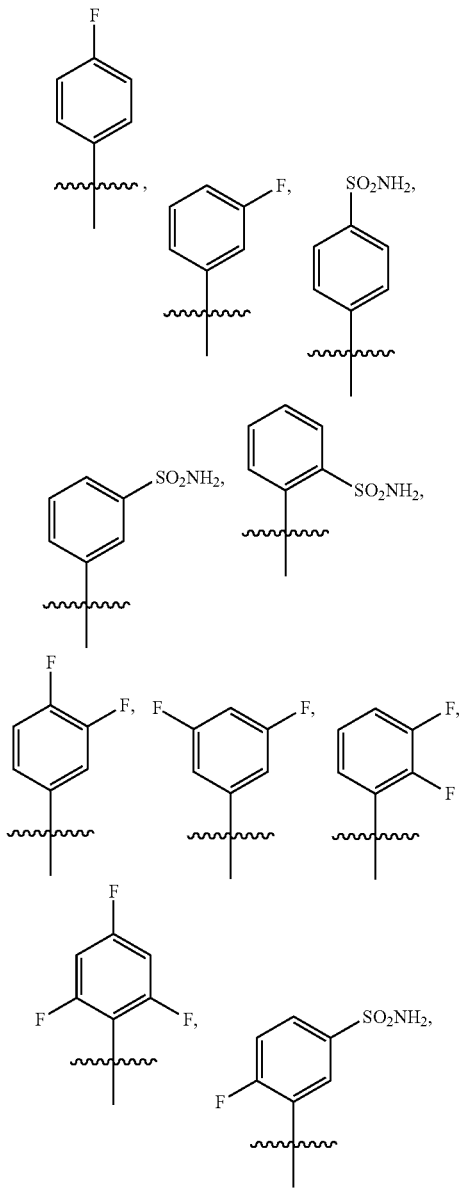

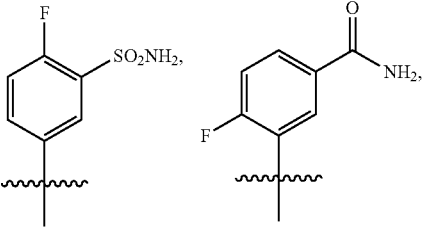

or an aryl substituted with one or more trifluoromethyl groups;
R³ is H;
or —N(R²)(R³) is

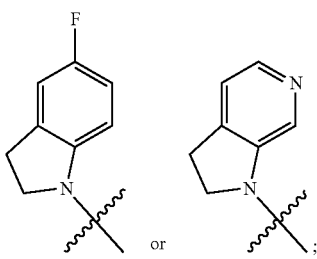 [SMILES: *N1CCc2cc(F)ccc21 ; *N1CCc2ccncc21]

R⁴ is unsubstituted thiophenyl, unsubstituted pyridinyl, unsubstituted oxazolyl, or unsubstituted thiazolyl; and
X¹ is —C(O)—, —C(NH)—, —C(S)—, or —S(O)₂—.

2. The compound of claim 1, wherein X¹ is —C(O)—.

3. A composition comprising a compound of claim 1 and a pharmaceutically acceptable carrier.

4. A pharmaceutical composition for treating an enterovirus, paramyxovirus, respiratory virus, flaviviridae virus, bunyaviridae virus, togaviridae virus, or rabies virus infection, the composition comprising an effective amount of the compound of claim 1 and a pharmaceutically acceptable excipient.

5. A method for inhibiting the replication of an enterovirus, paramyxovirus, respiratory virus, flaviviridae virus, bunyaviridae virus, togaviridae virus, or rabies virus in a cell infected with the enterovirus, paramyxovirus, respiratory virus, flaviviridae virus, bunyaviridae virus, togaviridae virus, or rabies virus, the method comprising contacting the cell with a compound of claim 1.

6. A method of inhibiting death of a cell infected with an enterovirus, paramyxovirus, respiratory virus, flaviviridae virus, bunyaviridae virus, togaviridae virus, or rabies virus, the method comprising contacting the cell with a compound of claim 1.

7. A method of treating a patient or animal infected with an enterovirus, paramyxovirus, respiratory virus, flaviviridae virus, bunyaviridae virus, togaviridae virus, or rabies virus, the method comprising administration of an effective amount of a compound of claim 1 to the patient or animal.

8. A compound according to Formula I:

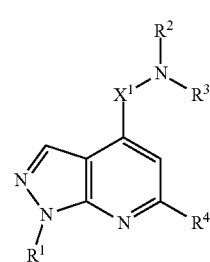

or a pharmaceutically acceptable salt thereof;
wherein:

R¹ is isopropyl;

R² is

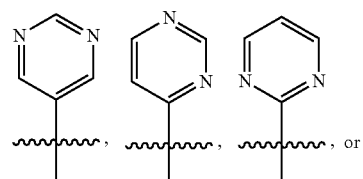, or

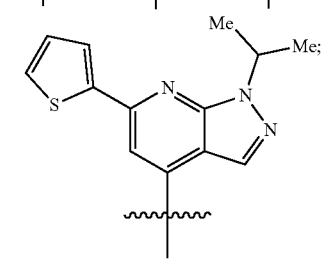

R³ is H;

R⁴ is cycloalkyl, phenyl, thiophenyl, pyridinyl, oxazolyl, or thiazolyl; and

X' is —C(O)—, —C(NH)—, —C(S)—, or —S(O)₂—.

9. A composition comprising a compound of claim 8 and a pharmaceutically acceptable carrier.

10. A pharmaceutical composition for treating an enterovirus, paramyxovirus, respiratory virus, flaviviridae virus, bunyaviridae virus, togaviridae virus, or rabies virus infection, the composition comprising an effective amount of the compound of claim 8 and a pharmaceutically acceptable excipient.

11. A method for inhibiting the replication of an enterovirus, paramyxovirus, respiratory virus, flaviviridae virus, bunyaviridae virus, togaviridae virus, or rabies virus in a cell infected with the enterovirus, paramyxovirus, respiratory virus, flaviviridae virus, bunyaviridae virus, togaviridae virus, or rabies virus, the method comprising contacting the cell with a compound of claim 8.

12. A method of treating a patient or animal infected with an enterovirus, paramyxovirus, respiratory virus, flaviviridae virus, bunyaviridae virus, togaviridae virus, or rabies virus, the method comprising administration of an effective amount of the compound of claim 8 to the patient or animal.

13. The compound of claim 1, wherein the compound is

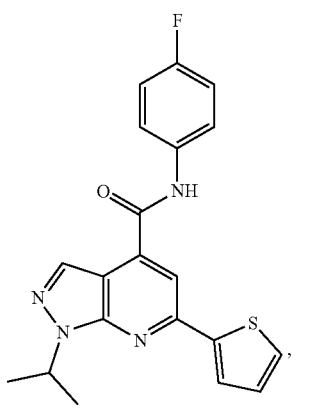

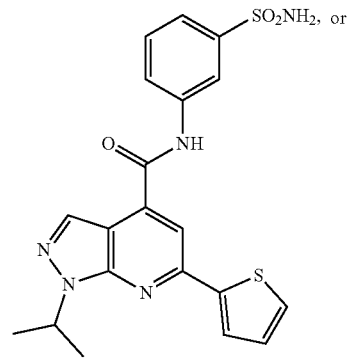

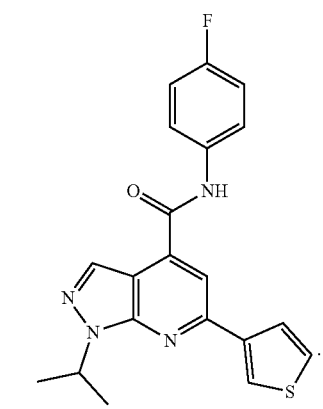

14. The compound of claim 8, wherein the compound is

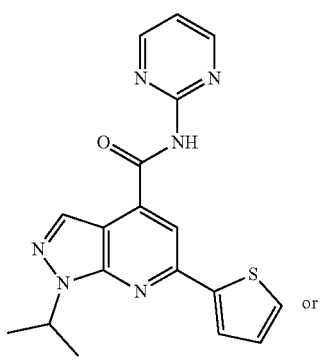

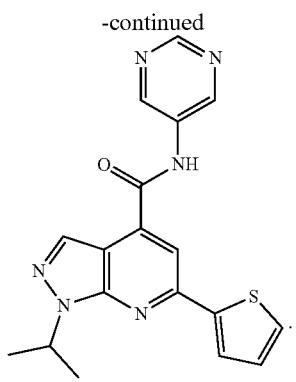

15. A pharmaceutical composition for treating an enterovirus, paramyxovirus, respiratory virus, flaviviridae virus, bunyaviridae virus, togaviridae virus, or rabies virus infection, the composition comprising an effective amount of the compound of claim 13 and a pharmaceutically acceptable excipient.

16. A method for inhibiting the replication of an enterovirus, paramyxovirus, respiratory virus, flaviviridae virus, bunyaviridae virus, togaviridae virus, or rabies virus in a cell infected with the enterovirus, paramyxovirus, respiratory virus, flaviviridae virus, bunyaviridae virus, togaviridae virus, or rabies virus, the method comprising contacting the cell with a compound of claim 13.

17. A method of treating a patient or animal infected with an enterovirus, paramyxovirus, respiratory virus, flaviviridae virus, bunyaviridae virus, togaviridae virus, or rabies virus, the method comprising administration of an effective amount of a compound of claim 13 to the patient or animal.

18. A pharmaceutical composition for treating an enterovirus, paramyxovirus, respiratory virus, flaviviridae virus, bunyaviridae virus, togaviridae virus, or rabies virus infection, the composition comprising an effective amount of the compound of claim 14 and a pharmaceutically acceptable excipient.

19. A method for inhibiting the replication of an enterovirus, paramyxovirus, respiratory virus, flaviviridae virus, bunyaviridae virus, togaviridae virus, or rabies virus in a cell infected with the enterovirus, paramyxovirus, respiratory virus, flaviviridae virus, bunyaviridae virus, togaviridae virus, or rabies virus, the method comprising contacting the cell with a compound of claim 14.

20. A method of treating a patient or animal infected with an enterovirus, paramyxovirus, respiratory virus, flaviviridae virus, bunyaviridae virus, togaviridae virus, or rabies virus, the method comprising administration of an effective amount of a compound of claim 14 to the patient or animal.

* * * * *